(12) United States Patent
Obata et al.

(10) Patent No.: US 11,773,368 B2
(45) Date of Patent: Oct. 3, 2023

(54) CULTURE METHOD FOR DIFFERENTIATING PRIMORDIAL GERM CELLS INTO FUNCTIONALLY MATURE OOCYTES

(71) Applicants: TOKYO UNIVERSITY OF AGRICULTURE, Tokyo (JP); NATIONAL AGRICULTURE AND FOOD RESEARCH ORGANIZATION; KYUSHU UNIVERSITY, NATIONAL UNIVERSITY CORPORATION, Fukuoka (JP)

(72) Inventors: Yayoi Obata, Tokyo (JP); Yuji Hirao, Tsukuba (JP); Katsuhiko Hayashi, Fukuoka (JP)

(73) Assignees: NATIONAL AGRICULTURE AND FOOD RESEARCH ORGANIZATION, Ibariki (JP); KYUSHU UNIVERSITY, NATIONAL UNIVERSITY CORPORATION, Fukuoka (JP); TOKYO UNIVERSITY OF AGRICULTURE EDUCATIONAL CORPORATED, Tokyo (JP)

( * ) Notice: Subject to any disclaimer, the term of this patent is extended or adjusted under 35 U.S.C. 154(b) by 320 days.

(21) Appl. No.: 15/760,525

(22) PCT Filed: Sep. 16, 2016

(86) PCT No.: PCT/JP2016/077574
§ 371 (c)(1),
(2) Date: Mar. 15, 2018

(87) PCT Pub. No.: WO2017/047799
PCT Pub. Date: Mar. 23, 2017

(65) Prior Publication Data
US 2018/0251729 A1 Sep. 6, 2018

(30) Foreign Application Priority Data

Sep. 17, 2015 (JP) .................................. 2015-184513

(51) Int. Cl.
| | |
|---|---|
| *C12N 5/00* | (2006.01) |
| *C12N 5/075* | (2010.01) |
| *C12N 5/073* | (2010.01) |
| *C12N 15/09* | (2006.01) |

(52) U.S. Cl.
CPC ......... *C12N 5/0609* (2013.01); *C12N 5/0604* (2013.01); *C12N 15/09* (2013.01); *C12N 2500/90* (2013.01); *C12N 2501/30* (2013.01); *C12N 2501/392* (2013.01); *C12N 2501/998* (2013.01); *C12N 2506/02* (2013.01); *C12N 2506/04* (2013.01)

(58) Field of Classification Search
CPC .................................................. C12N 5/0609
See application file for complete search history.

(56) References Cited

U.S. PATENT DOCUMENTS

| | | | | |
|---|---|---|---|---|
| 7,671,027 B2 * | 3/2010 | Loumaye | ............. | A61K 31/381 514/1.1 |
| 2010/0285579 A1 * | 11/2010 | Lim | ..................... | C12N 5/0606 435/353 |
| 2014/0314762 A1 * | 10/2014 | Cheng | .................... | A61K 38/22 424/134.1 |

FOREIGN PATENT DOCUMENTS

CN 102363765 A 2/2012

OTHER PUBLICATIONS

Hayashi, K et al. Offspring from oocytes derived from in vitro primordial germ cell-like cells in mice. Science. 2012. 338: 971-975. (Year: 2012).*
Picton et al., Reproduction 2008, 136:703-715 (Year: 2008).*
Clark et al., Journal of Reproductive Immunology 2014, 103:1-8 (Year: 2014).*
Neubar et al., Human Reproduction 2000, 15(1)171-174 (Year: 2000).*
Schmidt et al., Journal of Reproductive Immunology 2015, 108:65-71 (Year: 2015).*
Telfer et al., Int. J. Dev. Biol. 2012, 56:901-907 (Year: 2012).*
Sasaki et al. Cell Stem Cell, Aug. 6, 2015, 17:178-194 (Year: 2015).*

* cited by examiner

*Primary Examiner* — James D Schultz
*Assistant Examiner* — James Joseph Graber
(74) *Attorney, Agent, or Firm* — WCF IP

(57) ABSTRACT

A problem of this invention it to provide a method for differentiate a primordial germ cell into a functional GV stage oocyte by in vitro culture.

This invention relates to a method for differentiating a primordial germ cell into a functional GV stage oocyte by in vitro culture, comprising: (a) a step of producing a secondary follicle by culturing the primordial germ cell and supporting cells adjacent to the primordial germ cells under conditions that eliminate the effects of estrogen or a factor having a similar function to estrogen; (b) a step of partially dissociating cells between a granulosa cell layer and a thecal cell layer, wherein an oocyte, the granulosa cell layer, and the thecal cell layer constitute the produced secondary follicle; and (c) a step of differentiating the oocyte into a functional GV stage oocyte by culturing the oocyte, the granulosa cell layer, and the thecal cell layer that constitute the secondary follicle in a medium containing a high-molecular-weight compound.

4 Claims, 13 Drawing Sheets

Specification includes a Sequence Listing.

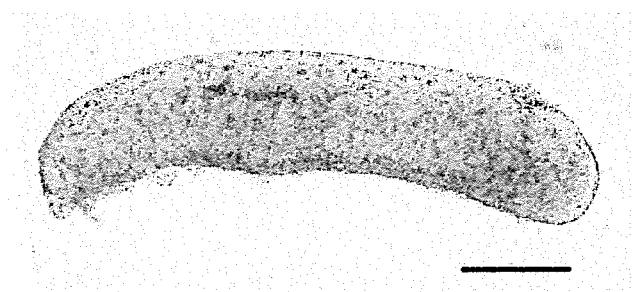
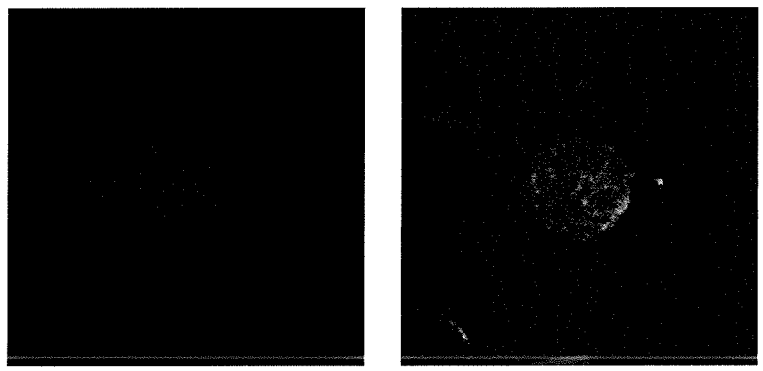
FIGURE 1

| Embryonic age and age in days | dpc | | | | | | | dpp | | | | | | | | | | |
|---|---|---|---|---|---|---|---|---|---|---|---|---|---|---|---|---|---|---|
| | 12.5 | 13.5 | 14.5 | 15.5 | 16.5 | 17.5 | 18.5 | 0 | 1 | 2 | 3 | 4 | 5 | 6 | 7 | 8 | 9 | 10 |
| | 0 | 1 | 2 | 3 | 4 | 5 | 6 | 7 | 8 | 9 | 10 | 11 | 12 | 13 | 14 | 15 | 16 | 17 |
| Events in oogenesis | ▲ ☐ Meiosis entry ▲▲▲ | | | | | ▲▲ Oocyte cyst breakdown ▲▲▲▲▲ | | | | | ▲ Arrest at a diplotene stage of first meiosis ▲▲▲▲▲▲▲▲▲▲▲▲▲▲▲▲▲▲▲▲▲▲▲▲▲▲▲▲▲▲▲▲▲ | | | | ▲ Primordial follicle ▲▲ formation ▲▲ | | | | |
| Test section | Substances added to medium and periods of the addition thereof | | | | | | | | | | | | | | | | | |
| FBS | 10% FBS | | | | | | | | | | | | | | | | | |
| SPS | 10% SPS | | | | | | | | | | | | | | | | | |
| KSR | 10% KSR | | | | | | | | | | | | | | | | | |
| FBS/SPS | 10% FBS | | | | | | | 10% SPS | | | | | | | 10% FBS | | | |
| FBS/10 nM ICI | 10% FBS | | | | | | | 10% FBS + 10 nM ICI | | | | | | | 10% FBS | | | |
| FBS/100 nM ICI | 10% FBS | | | | | | | 10% FBS + 100 nM ICI | | | | | | | 10% FBS | | | |
| FBS/1 μM ICI | 10% FBS | | | | | | | 10% FBS + 1 μM ICI | | | | | | | 10% FBS | | | |
| FBS/5 μM ICI | 10% FBS | | | | | | | 10% FBS + 5 μM ICI | | | | | | | 10% FBS | | | |
| FBS/10 μM ICI | 10% FBS | | | | | | | 10% FBS + 10 μM ICI | | | | | | | 10% FBS | | | |
| FBS/1 μM Tamoxifen | 10% FBS | | | | | | | 10% FBS + 1 μM Tamoxifen | | | | | | | 10% FBS | | | |
| FBS/1 μM MPP | 10% FBS | | | | | | | 10% FBS + 1 μM MPP | | | | | | | 10% FBS | | | |

FIGURE 2

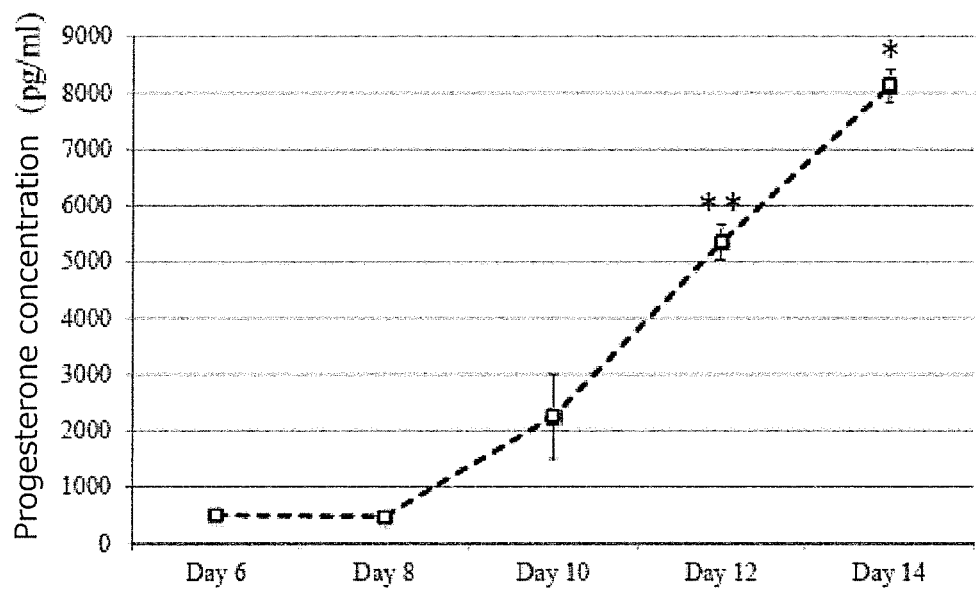
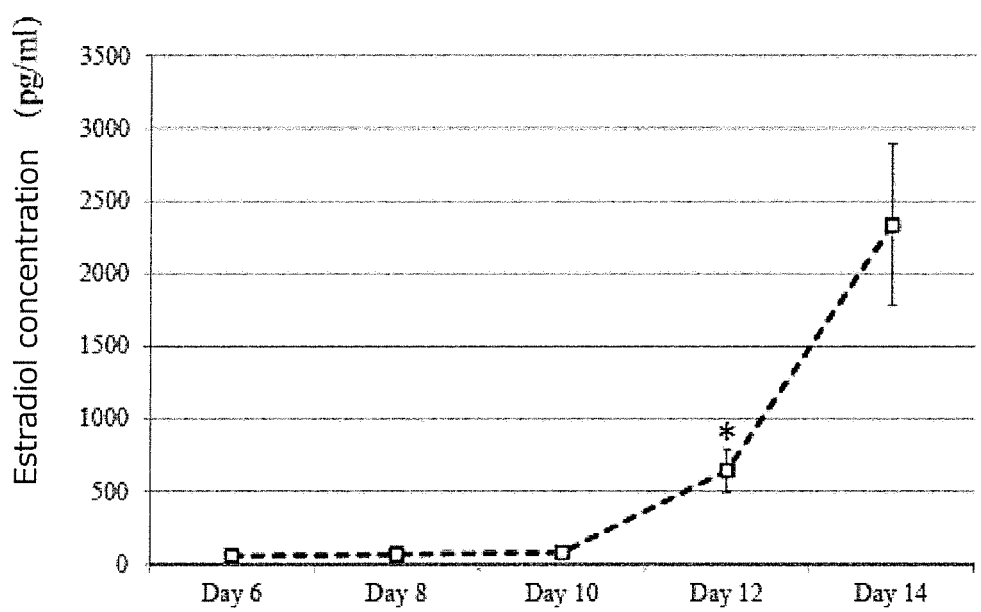
FIGURE 8

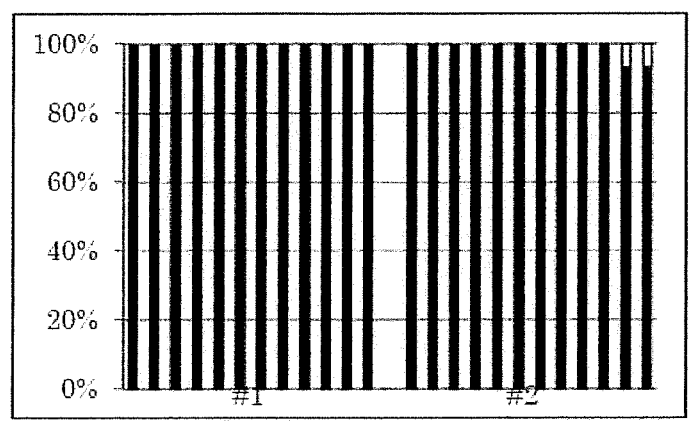
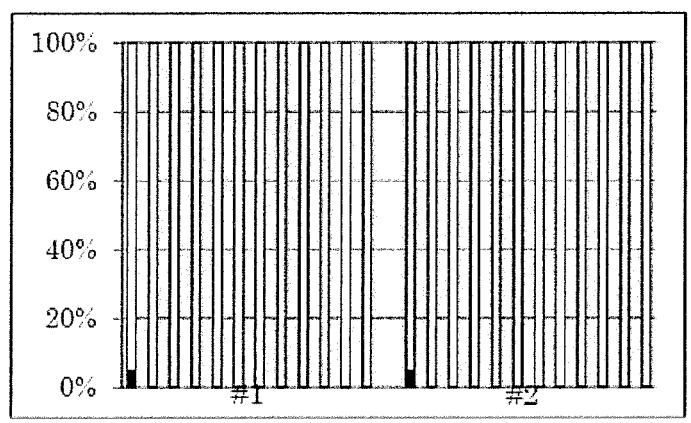
FIGURE 9

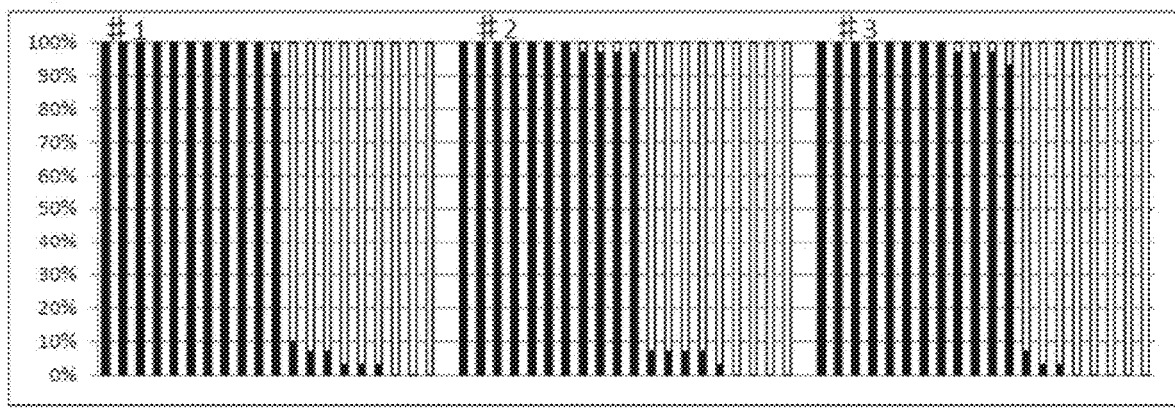
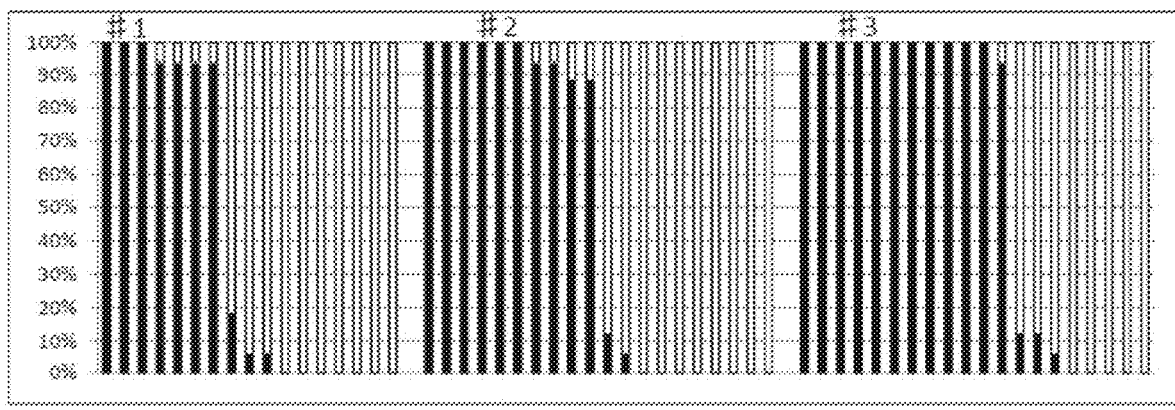
FIGURE 10

*Snrpn*
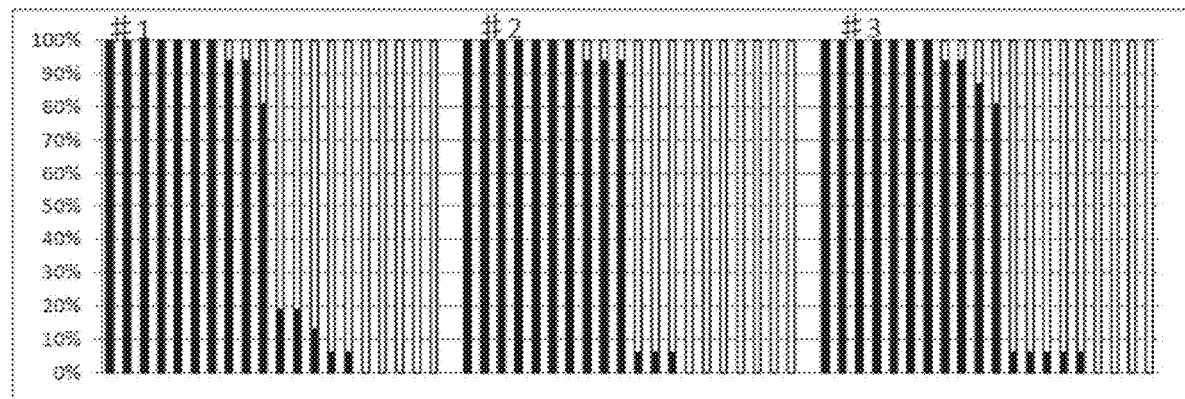
*Peg1/Mest*
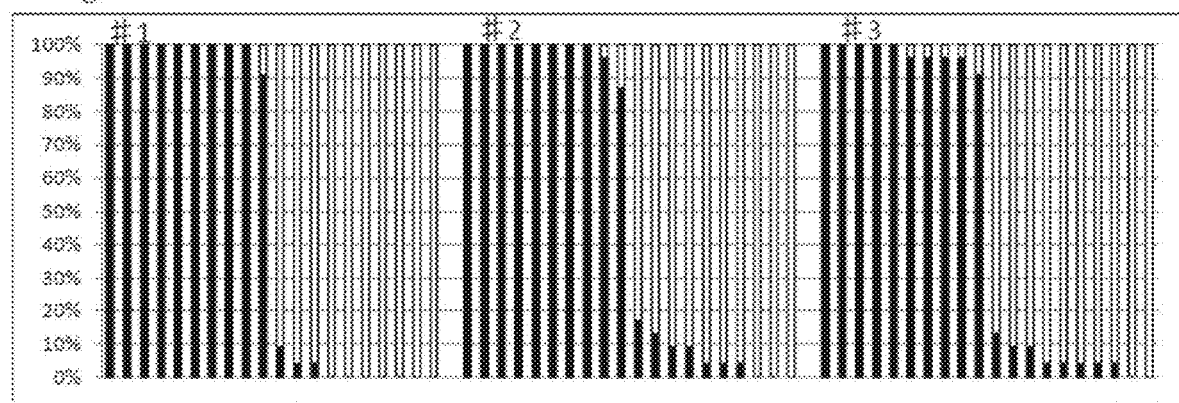
*H19*
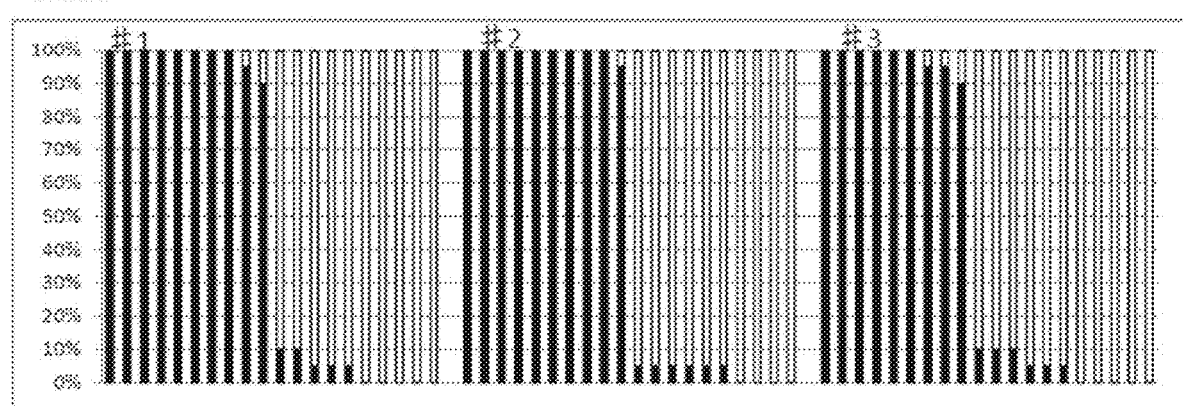
FIGURE 10 cont.

CULTURE METHOD FOR DIFFERENTIATING PRIMORDIAL GERM CELLS INTO FUNCTIONALLY MATURE OOCYTES

TECHNICAL FIELD

The present invention relates to a culture method for differentiating a primordial germ cell into a functionally mature oocyte.

BACKGROUND ART

Only germ cells can pass genetic information to the next generations. Furthermore, an egg of the germ cells plays a role of initiating development and leading the early development, and thus, the egg is in charge of a very important primary role. A large number of primordial germ cells in the mitotic stage are present in a fetal gonad of a mammalian female. Before birth, they all shift to the meiosis and differentiate into oocytes. Having shifted to meiosis, the oocytes cannot proliferate again, and the oocytes in the ovary are in an arrested developmental stage. Depending on an estrous cycle and the number of ovulations unique to animal species, only apart of the oocytes can grow and maturate. Accordingly, the number of fertile eggs produced by females in their lifetime is very small compared with the number of primordial germ cells and sperms as male germ cell (see Non-Patent Literatures 1 and 2). Also, the detailed mechanism of differentiation into functional eggs has not yet been clarified. In light of the foregoing, an establishment of an in vitro culture method for differentiating primordial germ cells into eggs can be one approach to overcoming the above problem in oogenesis. Also, the establishment of such an in vitro culture system ensures a new resource of eggs. For now, however, there are no reports that female primordial germ cells before meiosis and immature oocytes before folliculogenesis could successfully differentiate into functional eggs (that is, ones capable of producing offspring) by in vitro culture. This is due to the fact that a follicle formation required to sufficient support of the differentiation into eggs, and oocyte growth and maturation have not been yet reproduced under culture conditions.

Some in vitro culture systems for producing fully functional eggs from primordial germ cells have been proposed, but those systems have not yet reached full-term development because of an abnormal follicle formation and insufficient oocyte growth.

For example, Non-patent literature 3 discloses a method for enhancing efficiency in the differentiation into oocytes in the metaphase of second meiosis by culturing a part of female mouse gonad 12.5 days post coitum (dpc) embryos (fetal ovaries) of female mice in the presence of Activin A and then by co-culturing the oocytes with preantral granulosa cells (PAGCs). However, there are no reports that eggs obtained by the method of Non-patent literature 3 could develop to mouse offspring.

In mice, there is another report that the 12.5-dpc fetal gonads were transplanted in adult female mice and that secondary follicles taken 14 days after the transplantation differentiated into functional eggs capable of producing offspring by in vitro culture(see Non-Patent Literature 4). Recently, primordial germ cell-like cells have been produced from ES cells and iPS cells by in vitro culture. As also reported, these cells were co-cultured with 12.5-dpc gonadal somatic cells to produce cell aggregates, and they were transplanted inside of the mouse body to differentiate into functional oocytes capable of producing offspring (see Non-Patent Literature 5). In Non-Patent Literatures 4 and 5, however, target cells are necessary to be transplanted inside of the mouse body in order to bring about meiosis and folliculogenesis and to obtain mature oocytes. That means, an individual mouse is required for the oocyte growth, and oocytes are not fully maturated by in vitro culture.

Non-patent literature 1 discloses an oocyte culture method including a step of culturing a complex of oocytes and its peripheral somatic cells in the presence of a high-molecular-weight compound. The method in non-patent literature 1 can efficiently mature oocytes isolated from adult ovaries in vitro. However, the method in non-patent literature 1 includes a step of obtaining oocytes arrested at prophase in first meiosis by collecting oocyte-granulosa cell complexes from developing follicles in a living body and a step of performing in vitro-growth and in vitro-maturation of the obtained oocytes. This means that the method is not one comprising a step of initiating in vitro culture with primordial germ cells.

Thus, at this time, there are no reports on a method enabling primordial germ cells or primordial germ cell-like cells to develop to the functional oocytes without using the living body. If any method enables mammalian primordial germ cells before meiosis to develop to the functional oocytes by in vitro culture, the method ensures a huge amount of oocytes. The method would be also helpful to visualize and understand of a complicated mechanisms of oogenesis. Therefore, the method which can produce functional oocytes from the primordial germ cells by in vitro culture was desired.

PRIOR ART

Patent Literature

[Patent literature 1] Japanese Unexamined Patent Application Publication No. 2004-173635

Non-Patent Literature

[Non-patent literature 1] Tam, P. P. & Snow, M. H. "Proliferation and migration of primordial germ cells during compensatory growth in mouse embryos." J Embryol Exp Morphol 64, 133-147 (1981)

[Non-patent literature 2] Miyano, T. JSAR Outstanding Research Award. "In vitro growth of mammalian oocytes." J Reprod Dev 51, 169-176 (2005)

[Non-patent literature 3] Zhang, Z. P. et al., "Growth of Mouse Oocytes to Maturity from Premeiotic Germ Cells In vitro" PLoS One 7, e41771 (2012)

[Non-patent literature 4] Shen W, Zhang D, Qing T, Cheng J, Bai Z, Shi Y, Ding M, Deng H., "Live offspring produced by mouse oocytes derived from premeiotic fetal germ cells." Biol Reprod 75, 615-623 (2006)

[Non-patent literature 5] Hayashi K., et al, "Offspring from Oocytes Derived from in vitro Primordial Germ Cell-like Cells in Mice." Science 338, 971-975 (2012)

SUMMARY OF INVENTION

Problem to be Solved by the Invention

The problem of this invention is to provide a method for differentiating a primordial germ cell into a functional oocyte. Also, the problem of this invention is to provide a method for obtaining functional eggs from the oocytes obtained by the differentiation method.

Means for Solving the Invention

In order to solve the above problems, the inventors of the present invention studied on an ovarian culture method to enhance initial events such as meiosis, folliculogenesis, and follicle growth. First, 12.5 dpc fetal gonad was cultured in a 10% FBS-containing alpha-MEM medium on Transwell®-COL for 17 days by an air-liquid interface method (Trowell, O. A. "The culture of mature organs in a synthetic medium." Exp Cell Res 16, 118-147 (1959)), as known standard culture conditions.

SCP3, a meiosis marker, in the 12.5 dpc fetal gonad was immunostained, and SCP3-positive cells were not detected. However, at day 5 of the culture, a number of SCP3-positive cells were detected, regardless of co-culture with mesonephros. This means that oocytes can initiate meiosis even in vitro culture. For a continuous oocyte growth at a later stage from secondary follicle formation in ovary, a complicated vascularized-tissue and blood flow is required. However, since an in vitro-cultured ovaries do not have such tissue and blood flow, it is necessary to isolate secondary follicles and to culture them in vitro. On the other hand, having isolated secondary follicles from the ovary at day 17 of the culture, the inventors found that more than 100 growing oocytes were existed in one ovary. However, it was difficult to isolate follicles formed by the ovarian culture adopting known culture condition was difficult to be isolated. Normal follicles form a round structure in which the surface of the oocyte is surrounded by granulosa cell layer which is further surrounded by theca cell layer and grow. On the other hand, in cultured ovaries, the number of such round follicles is small, follicles is fragile, and when those follicles is isolated, a large number of oocytes became denuded. Laminin, a basal membrane-structural protein forming the follicle and granting strength thereto, in the ovary obtained by in vitro culture was immunohistochemically analyzed. The result shows that the basal membrane (laminin) was localized in a round shape surrounding a follicle when the ovary tissue derived from a mouse at 10 days after birth is cut in plane and observed. On the other hand, in in vitro cultured ovary, laminin was observed in a patches shape on the same plane, not forming a round shape. In addition, the abnormal formation of theca cell layer was remarkably observed, for instance, a part of theca cell population which typically exists in the exterior of the follicle independently exist to each follicle is shared by the follicle adjacent from side to side and up and down to each other, and a floral shaped-localization of laminin was observed (FIG. 5a). Therefore, a novel method enabling a follicle isolation was required.

Then, the inventors of this application focused on effects of sex steroid hormones (in particular, estrogen and a factor having a similar function to estrogen) in culture medium during in vitro culture of the gonad. As a result of intensive studies, the inventor found that a method including a step of eliminating the effects of estrogen and the factor having the similar function to estrogen in the medium for the gonad culture can produce secondary follicles in large numbers, essentially required for the differentiation into functional eggs.

Additionally, the inventor studied on in vitro organ culture of the obtained secondary follicles. As a result, the inventor found that functionally mature oocytes could be produced by the method including a step of partially dissociating cells between a granulosa cell layer and a theca cell layer in follicles when secondary follicles are cultured in vitro and a step of culturing oocyte-granulosa cell complexes in the medium containing a high-molecular-weight compound.

One aspect of this invention relates to:

[1] A method for differentiating a primordial germ cell into a functional GV stage oocyte by in vitro culture, comprising:
(a) a step of producing a secondary follicle by culturing the primordial germ cell and supporting cells adjacent to the primordial germ cells under conditions that eliminate the effects of estrogen or a factor having a similar function to estrogen;
(b) a step of partially dissociating cells between a granulosa cell layer and a thecal cell layer, wherein an oocyte, the granulosa cell layer, and the thecal cell layer constitute the produced secondary follicle; and
(c) a step of differentiating the oocyte into the functional GV stage oocyte by culturing the oocyte, the granulosa cell layer, and the thecal cell layer that constitute the secondary follicle in a medium containing a high-molecular-weight compound.

One embodiment of the method for differentiating the primordial germ cell into the functionally mature GV stage oocyte by in vitro culture according to this invention is characterized in that:

[2] the culture under conditions that eliminate the effects of estrogen or the factor having a similar function to estrogen in the step (a) comprises culturing in the presence of an estrogen inhibitor or culturing using a serum-free medium.

One embodiment of the method for differentiating the primordial germ cell into the functionally mature GV stage oocyte by in vitro culture according to this invention is characterized in that:

[3] the estrogen inhibitor used in the step (a) is an estrogen receptor antagonist.

One aspect according to this invention relates to:

[4] A method for differentiating a primordial germ cell into a functionally mature GV stage oocyte by in vitro culture, comprising:
(a) a step of producing the secondary follicle by culturing the primordial germ cell and supporting cells adjacent to the primordial germ cells under conditions that eliminate the effects of sex steroid hormone or a factor having a similar function to sex steroid hormone;
(b) a step of partially dissociating cells between a granulosa cell layer and a thecal cell layer, wherein an oocyte, the granulosa cell layer, and the thecal cell layer constitute the produced secondary follicle; and
(c) a step of differentiating the oocyte into the functional GV stage oocyte by culturing the oocyte, the granulosa cell layer, and the thecal cell layer that constitute the secondary follicle in a medium containing a high-molecular-weight compound.

One embodiment of the method for differentiating the primordial germ cell into the functionally mature GV stage oocyte by in vitro culture according to this invention is characterized in:

[5] the method according to the above [4], wherein the culture under conditions that eliminate the effects of sex steroid hormone or the factor having a similar function to sex steroid hormone in the step (a) comprises culturing in the presence of an sex steroid hormone-inhibitor or culturing using a serum-free medium.

One embodiment of the method for differentiating the primordial germ cell into the functionally mature GV stage oocyte by in vitro culture according to this invention is characterized in:

[6] the method according to the above [5], wherein the sex steroid hormone-inhibitor is an estrogen inhibitor or an androgen inhibitor, or a combination thereof.

One embodiment of the method for differentiating the primordial germ cell into the functionally mature GV stage oocyte by in vitro culture according to this invention is characterized in:

[7] the method according to any one of the above [1] to [6], wherein the partial dissociation of the cell layers in the step (b) is carried out by enzymatic treatment and/or by physical means.

One embodiment of the method for differentiating the primordial germ cell into the functionally mature GV stage oocyte by in vitro culture according to this invention is characterized in:

[8] the method according to any one of the above [1] to [7], wherein in the step (c), the high-molecular-weight compound is at least one compound selected from the group consisting of polyvinylpyrrolidone, Ficoll®, hydroxypropylmethyl cellulose, and serum albumin.

The method for differentiating the primordial germ cell into the functionally mature GV stage oocyte by in vitro culture of this invention includes a combination of two or more features described in embodiments according to any one of the above [1] to [8].

One aspect according to this invention relates to:

[9] A GV-stage oocyte obtained by the method according to any one of the above [1] to [8].

One aspect according to this invention relates to:

[10] A method for producing a functional egg, comprising: a step of subjecting a GV-stage oocyte obtained by the method according to any of Claims 1 to 5 to in vitro maturation culture to resume meiosis.

One aspect according to this invention relates to:

[11] An egg obtained by the method according to any one of the above [10].

One aspect according to this invention relates to:

[12] A kit for differentiation of a primordial germ cell into a functional egg in vitro, comprising: an estrogen inhibitor, a serum-free medium, a serum replacement, an enzyme for dissociating cells, or a high-molecular-weight compound, or a combination thereof.

One aspect according to this invention relates to:

[13] A kit for differentiation of a primordial germ cell into a functional egg in vitro, comprising: a sex steroid hormone-inhibitor, a serum-free medium, a serum replacement, an enzyme for dissociating cells, or a high-molecular-weight compound, or a combination thereof.

The property of the GV-stage oocyte or the egg obtained by the method according to the above [9] or [11] is different from that of the GV-stage oocyte or the egg obtained by known in vitro-culture method. However, it takes a long time to clarify such differences in property between them. Taking into account importance of rapidity on a patent application system, it is impractical to wait for the completion of clarifying such differences. Thus, the GV-stage oocyte or the egg according to the above [9] and [11] is specified by the method for producing thereof.

Effects of Invention

According to the method of this invention, the method is two-step culture method in which the primordial germ cell is used as a starting material, comprising a step of culturing a primordial germ cell before meiosis or the gonad only comprising the primordial germ cells and a step of subjecting a secondary follicle obtained by the culture to in vitro maturation, and functionally mature oocyte can be obtained by the method. For example, the method of this invention can produce mature eggs in about one month from primordial germ cells in fetal mouse-derived gonads.

BRIEF DESCRIPTION OF THE DRAWINGS

FIG. 1a is the image showing a 12.5-dpc female fetal mouse derived-gonad. FIG. 1b is images showing female primordial germ cells derived from an ovary at day 0 of the culture (left side) and a cell at day 5 of the culture without mesonephros (right side) which processed for immunostaining with anti-SCP3 antibody. The nucleus was stained with DAPI. SCP3, a meiosis marker, was negative at day 0 of the culture. On the other hand, SCP3 was positive at day 5 of the culture, which means primordial germ cells differentiated into oocytes.

FIG. 2 explains each of the experimental conditions in "1. In vitro organ culture of gonad" of the example described below.

FIGS. 3a to 3d respectively shows the ovaries obtained by culturing under each conditions of (i) FBS group (FIG. 3a), (ii) SPS group (FIG. 3b), (iv) FBS/SPS group (FIG. 3c), or (v) FBS/10 μM ICI group (FIG. 3d) described in Example 1 below.

FIG. 8 is the graph showing capacity for producing steroid hormone measured with an enzyme immunoassay kit (Cayman), when the follicles obtained by the organ culture of (v) FBS/10 μM ICI group were cultured in the method in "3. In vitro culture of secondary follicle" of the example below. A significant difference in the concentration of steroid hormone is determined by t-test. *(asterisk) stands for a significant fluctuation of the measurement value of steroid hormone compared to that at 2 days ago (*$P<0.05$, **$P<0.01$). Error bar indicates standard deviation (n=4).

FIG. 9 shows the result on a methylation state of imprinting genes (Igf2r and H19) in oocytes obtained in "3. In vitro culture of secondary follicle" described below by bisulfite method. Igf2r is an imprinted gene subject to maternal allele-specific hypermethylation. H19 is an imprinted gene subject to paternal allele-specific hypermethylation. Bar in a bar graph respectively shows analyzed DNA strands, black part in bar shows a rate of methylated CpG sites in the analyzed DNA strands, and white part in bar shows a rate of non-methylated CpG sites in the analyzed DNA strains. #1 and #2 samples are different and independent to each other.

FIG. 10 shows the result on a methylation state of imprinted genes (Igf2r, H19, Lit1, Snrpn, and Peg1/Mest) in offspring obtained in "8. In vitro fertilization of in vitro mature oocyte and embryo transfer" in which eggs obtained by the method in "3. In vitro culture of secondary follicle" and "6. Maturation to egg by in vitro culture" described below by bisulfite method. Igf2r, Lit1, Snrpn, and Peg1/Mest are imprinted genes subject to maternal allele-specific hypermethylation. H19 is an imprinted gene subject to paternal allele-specific hypermethylation. Bar in a bar graph respectively shows analyzed DNA strands black part in bar shows a rate of methylated CpG sites in the analyzed DNA strands, and white part in bar shows a rate of non-methylated CpG sites in the analyzed DNA strands. #1 and #2 samples are different and independent to each other. #3 sample is control (offspring developed from a living body derived-oocyte by the same method).

FIG. 14D shows COCs isolated from the grown secondary follicle at 11$^{th}$ day from starting the culture method.

FIG. 14E shows the image under an optical microscope of mature eggs (MII stage) obtained by the method described in "II-5. In vitro maturation (IVM) into oocyte by in vitro culture" of "10. In vitro culture method for producing functional GV-stage oocytes and functional eggs with PGCLC derived from pluripotent stem cells" described below.

DESCRIPTION OF EMBODIMENTS

Figure 3:
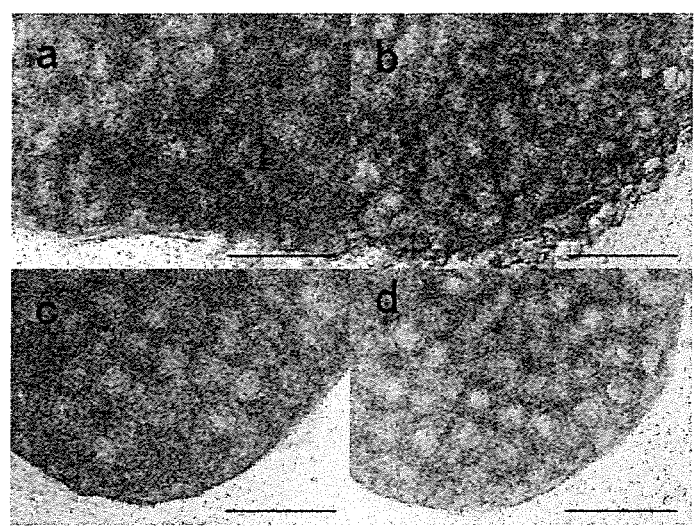
FIG. 3 is images under an optical microscope showing the ovaries obtained by in vitro-culturing a 12.5-dpc fetal mouse-derived gonad under conditions described in Example 1 described below.

One aspect according to this invention is a method for differentiating a primordial germ cell into a functionally mature GV stage oocyte by in vitro culture, comprising:
(a) a step of producing a secondary follicle by culturing the primordial germ cell and supporting cells adjacent to the primordial germ cells under conditions that eliminate the effects of sex steroid hormone (for example, estrogen or a factor having a similar function to estrogen);
(b) a step of partially dissociating cells between a granulosa cell layer and a thecal cell layer among an oocyte, the granulosa cell layer, and the thecal cell layer that constitute the produced secondary follicle; and
(c) a step of differentiating the oocyte into a functional GV stage oocyte by culturing the oocytes, the granulosa cell layer, and the thecal cell layer that constitute the secondary follicle in a medium containing a high-molecular-weight compound.

In this specification, the term "primordial germ cell" means a cell being to differentiate into a germ cell and a cell being to differentiate into an egg or a sperm through an oogonia or a spermatogonia.

The primordial germ cell may be one derived from a living body and may be a primordial germ cell like cell (PGCLC) differentiated from a pluripotent stem cell. When the primordial germ cell is collected from the living body, for instance, the primordial germ cell can be collected together with the gonad from the female fetal mouse (11.5 to 12.5 dpc). When the gonad is collected from the living body, it can be collected with mesonephros accompanying or mesonephros can be disconnect from the gonad. The "primordial germ cell" used for this invention includes a primary oocyte which is differentiated from a primordial germ due to its developmental stage progress and whose meiosis initiates. The primary oocyte used for this invention is one before the onset of folliculogenesis.

As mentioned above, in this specification, the term "primordial germ cell" includes a primordial germ cell like cell (PGCLC) differentiated from a pluripotent stem cell. The term "pluripotent stem cell" means an undifferentiated cell having "self-renewal capability" to proliferate maintaining the undifferentiated state and "pluripotent differentiation capability" to differentiate into all types of ectodermal cell, endodermal cell, and mesodermal cell. The "pluripotent stem cell" includes, but not limited to, for example induced a pluripotent stem cell (iPS cell), an embryonic stem cell (ES cell), embryonic germ cell derived from primordial germ cell (EG cell), a multipotent germline stem cell which can be isolated in a culture process for establishing GS cells from a testis tissue (mGS cell), Muse cell occurred by nuclear reprogramming of ES cells or somatic cells. The above mentioned pluripotent stem cell can be obtained by known methods.

The iPS cell is the cell to which some genes are introduced and which has capability to be reprogrammed to various tissue cells or organ cells. In this invention, the iPS cell which can be used for the induction of the differentiation of the primordial germ cell may be one derived from a primary cultured cell of a somatic cell collected from an appropriate donor or one derived from an established cell line. Since iPS cell can differentiate into any ectodermal cell, endodermal cell, and mesodermal cell, the somatic cell used for preparation of the iPS cell can be essentially one derived from either type of the ectodermal cell and the endodermal cell. Cells from Skin, hair, gums, blood, and the like with less invasiveness which are easy to harvest is preferable as the somatic cell used for the preparation of the iPS cell in this aspect of this invention. The preparation method for iPS cell can be conducted according to known methods in this art. Concretely, for example, the preparation method disclosed in known literatures such as Okita K. et al, "Generation of germline-competent induced pluripotent stem cells." Nature 448, 313-317 (2007), Hamanaka S. et al., "Generation of germline-competent rat induced pluripotent stem cells" PLoS One 6(7), e22008 (2011), and Ohnuki M. et al., "Generation and characterization of human induced pluripotent stem cells." Curr Protoc Stem Cell Biol. June Chapter 4: Unit 4A.2, (2009) can be used.

In this invention, ES cells used for the induction of differentiation of the primordial germ cell is obtainable by known methods. For example, it can be established by collecting inner clump of cells from a blastocyst of a fertilized egg of a target animal and by culturing the inner clump of cells on feeder cells derived from fibroblast cells. In addition, ES cells established by culturing an early embryo produced by nuclear transfer with a somatic nucleus can be also used.

The method for inducing the differentiation of the iPS cell into the primordial germ cell can be performed by referring known methods such as Non-patent literature 5, Hayashi K. et al., "Reconstitution of the mouse germ cell specification pathway in culture by pluripotent stem cells." Cell, August 19, 146(4), 519-32 (2011), Hayashi K. et al., "Generation of eggs from mouse embryonic stem cells and induced pluripotent stem cells." Nature Protocols 8, 1513-1524 (2013); and Sasaki K. et al., "Robust In vitro Induction of Human Germ Cell Fate from Pluripotent Stem Cells." Cell Stem Cell July 1, pii: S1934-5909(15)00299-4, doi: 10.1016/j.stem.2015.06.014 (2015). The method for inducing the differentiation of the ES cell into the primordial germ cell can be performed by referring known methods such as Non-patent literature 5, Hayashi K., "Reconstitution of the mouse germ cell specification pathway in culture by pluripotent stem cells." Cell August 19, 146(4), 519-32 (2011), Nakaki et al., "Induction of mouse germ-cell fate by transcription factors in vitro" Nature, 501, 222-226 (2013), Kimura T. et al., "Induction of Primordial Germ Cell-Like Cells From Mouse Embryonic Stem Cells by ERK Signal Inhibition." Stem Cells 32, 2668-2678 (2014)

When PGCLCs derived from pluripotent stem cells are used as primordial germ cells, it is desirable to remove undifferentiated cells from the pluripotent stem cell population which processed for differentiation induction. Such method is known, for example those cells can be easily removed from the PGCLC population differentiated from pluripotent stem cells with a technique such as Fluorescence-activated cell sorting (FACS) by prospectively introducing a nucleic acid encoding a fusion protein comprising Blimp1, a primordial germ cell marker gene, and a reporter protein into pluripotent stem cells.

In this specification, the "primordial germ cell" includes the primordial germ cell derived from a living body and the primordial germ cell-like cell derived from the pluripotent stem cell which is modified by a method of genetic engineering as mentioned above.

As the method for genetically modifying the primordial germ cell derived from a living body and the primordial germ cell-like cell derived from the pluripotent stem cell, a target nucleic acid or a vector can introduce to those cells by using known method. For example, microinjection, electroporation, lipofection, or nucleic acid transfer with virus vector can be used. The method for introducing an external gene or an external nucleic acid fragment is not limited to the above method as long as the modified primordial germ cell can differentiate into the functional oocyte by the method of this invention.

One skilled in the art can perform a genetic modification against the primordial germ cell at an appropriate timing. For example, in mice, it can be performed during the period of 11.5 dpc to 12.5 dpc. When the primordial germ cells derived from the pluripotent stem cells were used, the pluripotent stem cells can be genetically modified by known methods before the induction of the differentiation into the primordial germ cells. Such genetic modification can be performed by reference to the method described in, for example, Watanabe et al., "Gene transfection of mouse primordial germ cells in vitro and analysis of their survival and growth control." Exp Cell Res 230, 76-83 (1997).

The term "supporting cell" means a cell surrounding the primordial germ cell and being to differentiate into a granulosa cell or a theca cell in the sexual-differentiated ovary. Since the supporting cell differentiates into the granulosa cell or the theca cell in the future, it can be used for co-culture with the primordial germ cell. Thus, the culture of the primordial germ cell is preferably performed by culturing a gonad itself or by co-culturing of the primordial germ cell and the supporting cell which contact with each other. When a PGCLC derived from the pluripotent stem cell is used as the primordial germ cell, the somatic cell derived from the gonad collected from the living body can be used as the supporting cell. When the somatic cell derived from the gonad collected from the living body is used as the supporting cell, the culture step of preliminarily producing an aggregate comprising PGCLC derived from the pluripotent stem cell and the somatic cell derived from the gonad is preferably added before "(a) the step of producing a secondary follicle by culturing a primordial germ cell and supporting cells adjacent to the primordial germ cells under conditions that eliminate the effects of sex steroid hormone (for example, estrogen or the factor having a similar function to estrogen)". The method for collecting the somatic cell derived from the gonad and the method for producing the aggregate comprising a PGCLC derived from the pluripotent stem cells and the somatic cells derived from the gonad can be performed according to the method in Non-patent literature 5. For example, the method for collecting the somatic cell derived from the gonad comprises surgically collecting a gonad and dissociating the somatic cells from the gonad with trypsin etc. In this method, it is preferable to remove germ cells internally existing in the living body-derived gonad. The method for removing those germ cells internally existing in the gonad can be performed by known methods. For example, those internally existing germ cells can be removed by magnetic activated cell sorting with anti-SSEA1 antibody or anti-CD31 antibody. The gonad for collecting the somatic cell as the supporting cell is preferably one derived from fetuses. In mice, for example, the gonad derived from a fetal mouse at 12.5 dpc is preferable. One skilled in the art can select the gonad at an appropriate stage depending on animal species derived therefrom based on the disclosure of this specification and the common knowledge in the art.

The method for producing the aggregate comprising a PGCLC derived from the pluripotent stem cell and the somatic cells derived from the gonad can be performed by mixing/aggregating a PGCLC derived from the pluripotent stem cell and the somatic cells derived from the gonad and by culturing those mixed and aggregated cells with GK15 medium containing retinoic acid (GMEM supplemented with 15% KSR, 1×GlutaMax, 1× penicillin/streptomycin (100 U/ml Penicillin and 0.1 mg/ml streptomycin), 100 µM 2-mercaptoethanol, and 1 µM retinoic acid). The culture plate with low adsorption property is preferably used for the culture. In mice, the culture period for producing the aggregate is for 2 to 3 days, preferably for 2 days. One skilled in the art can set the appropriate culture period depending on animal species. The ratio of mixing a PGCLC derived from the pluripotent stem cells and the somatic cells derived from the gonad is not limited as long as the produced aggregate can form the secondary follicle and the functional GV stage oocyte. For example, in mice, the ratio between the number of PGCLCs derived from the pluripotent stem cells and the number of the somatic cells derived from the gonad is preferably about 1:10.

The cryopreserved primordial germ cell, the cryopreserved supporting cell, or the cryopreserved gonad containing the primordial germ cell and the supporting cell can be also used. The cryopreservation method can be performed according to known methods. For example, the primordial germ cell and the supporting cell can be cryopreserved by slow freezing method with 10% DMSO medium or with cryopreservation agent commercially available (CELL-BANKER®), and the cryopreservation of the gonad can be performed according the method described in "9. Vitrification and thawing" of the example below.

The primordial germ cell which can be used for this invention is one derived from a mammal which is, not limited to, but such as pig, cow, horse, sheep, goat, dog, cat, rabbit, hamster, rat, mouse, and human.

The method of this invention comprises "(a) a step of producing a secondary follicle by culturing a primordial germ cell and supporting cells adjacent to the primordial germ cells under conditions that eliminate the effects of sex steroid hormone (for example, estrogen or a factor having a similar function to estrogen)".

In the step (a), the primordial germ cell and supporting cells adjacent to the primordial germ cells are cultured under conditions that eliminate the effects of sex steroid hormone (for example, estrogen or the factor having a similar function to estrogen). When the gonad collected from the living body is used, it is not necessary to isolate the primordial germ cell and the supporting cell from the gonad, and it is sufficient to culture the gonad as it is, the isolated aggregate of the isolated primordial germ cell and supporting cells, or some tissue sections. In this specification, the term "culturing a primordial germ cell and supporting cells adjacent to the primordial germ cells" in step (a) includes culturing the gonad containing the primordial germ cell and the supporting cell, the aggregate of the isolated primordial germ cell and the isolated supporting cells, or a part thereof. As long as the functional oocyte can be obtained, the primordial germ cell and the supporting cell can be isolated from the gonad and can be used for the culture. When the primordial germ cell-like cell derived from the pluripotent stem cell is used, it is preferable to prepare the aggregate comprising PGCLCs derived from the pluripotent stem cells and the somatic cells derived from the gonad preliminarily, as mentioned above. The term "primordial germ cell" may be a primary oocyte initiating meiosis and being in a state before forming a follicle. For that, the term "culturing a primordial germ cell" includes culturing the gonad containing the primary oocyte initiating meiosis and being in a state before forming follicle, the aggregate of the isolated primary oocyte and the supporting cells, or a part thereof.

In this specification, the term "estrogen" means one of sex steroid hormones which is generated from metabolism of androgen in the granulosa cell of the ovary. The released estrogen activates transcription of specific genes by binding to estrogen receptors. Three types of estrogen, estron (E1), estradiol (E2), and estriol (E3), are known. In this specification, the term "estrogen" includes those type of estrogen. Also, in this specification, the term "sex steroid hormone" includes androgens besides estrogen, such as testosterone, dihydrotestosterone, and androsterone.

"A Factor having a similar function to estrogen" or "a factor having a similar function to sex steroid hormone" is ones having the same function to estrogen or sex steroid hormone or a similar function to estrogen or sex steroid hormone. In this specification, the term "a similar function to estrogen" or "a similar function to sex steroid hormone" means at least one function in culturing the primordial germ cell, of (i) the function to inhibit the oocyte cyst breakdown in oocytes derived from the primordial germ cells and (ii) the function to inhibit the follicle formation. Such factor having a similar function to estrogen or sex steroid hormone includes, for example, factors which can bind to the sex steroid hormone receptor such as an estrogen receptor or an androgen receptor. In particular, such factor includes phenol red and the like. Since serum may include unidentified factors having a similar function to estrogen besides estrogen or androgen, the preferable embodiment can adopt the culture conditions which can eliminate the effects of such factors having a similar function to estrogen or sex steroid hormone.

The culture "under conditions that eliminate the effects of sex steroid hormone (for example, estrogen or a factor having a similar function to estrogen)" includes culturing in the presence of a "sex steroid hormone inhibitor". The "sex steroid hormone inhibitor" includes an androgen inhibitor, an estrogen inhibitor and a combination of the androgen inhibitor and the estrogen inhibitor. The "estrogen inhibitor" or the "sex steroid hormone inhibitor" which can be used for this invention is ones having the effect to inhibit the activation of the estrogen receptor or the sex steroid hormone receptor and comprise, for example, ICI 182,780 ((7R,9S,13S,14S,17S)-7-(9-(4,4,5,5,5-Pentafluoropentylsulfinyl)nonyl)-7,8,9,11,12,13,14,15,16,17-decahydro-13-methyl-6H-cyclopenta[a]phenanthrene-3,17-diol) which is the antagonist for the estrogen receptor. Also, the commercially available agents such as tamoxifen citrate, 4-hydroxytamoxifen, MPP (4-[1-(4-hydroxyphenyl)-4-methyl-5-[4-[2-(1-piperidinyl)ethoxy]phenyl]-1H-pyrazol-3-yl]-phenol) PHTPP (4-[2-Phenyl-5,7-bis(trifluoromethyl)pyrazolo[1,5-a]pyrimidin-3-yl]phenol), and G15 ((3aS,4R,9bR)-4-(6-Bromo-1,3-benzodioxol-5-yl)-3a,4,5,9b-3H-cyclopenta[c]quinoline) can be used as those inhibitors. In addition, the commercially available agents such as KW-365 (N-[4-[(Benzyl) (4-nitrophenyl)amino]-1-methylpyrrole-2-carbonyl]pyrrolidine) can be used as the estrogen inhibitor among the sex steroid hormone inhibitors. The estrogen inhibitor and the sex steroid hormone inhibitor are not limited to the above agents, and any inhibitor can be used as long as it has the effect to inhibit the activation of the estrogen receptor or the sex steroid hormone receptor and the effect to differentiate the primordial germ cell into the functional oocyte.

The inhibition of the activation of the estrogen receptor or the sex steroid hormone receptor control the oocyte cyst breakdown and/or the formation of primary follicles. Therefore, it is preferable to add the estrogen inhibitor at the timing before the oocyte cyst breakdown and/or the formation of primary follicles. It is not necessary to perform the culture "under conditions that eliminate the effects of sex steroid hormone (for example, estrogen or a factor having a similar function to estrogen)" from the onset of the culture of the primordial germ cell and the supporting cells adjacent to the primordial germ cell. It is preferable to perform the culture "under conditions that eliminate the effects of sex steroid hormone (for example, estrogen or a factor having a similar function to estrogen)" at least at the timing of the oocyte cyst breakdown and/or the formation of primary follicles.

The embodiment in which the estrogen inhibitor is used as the sex steroid hormone inhibitor and mice is used as animal species is explained below as an example: For example, in mice, almost oocyte cysts breakdown from 17.5 dpc to around the birth. Accordingly, it is preferable to add those inhibitors from the day of the culture corresponding to such embryonic age. When the gonad is collected at 12.5 dpc and the culture of the primordial germ cell starts from the collecting day, day 5 of in vitro culture corresponds to 17.5 dpc. The period for culturing in the medium containing the estrogen inhibitor can preferably set to the period for the completion of the oocyte cyst breakdown and the follicle formation. When the primordial germ cell from mice is cultured, it is not limited to, but preferable to culture the cells for 6 days from day 5 to day 11 of the culture. When the aggregate of the PGCLC derived from the mouse pluripotent stem cell and the somatic cells is cultured, it is not limited to, but preferable to culture the aggregate for 4 days from day 7 to day 10 of the culture counting from the onset of the culture of the aggregate preliminary prepared.

In above, although the embodiment using mouse is explained, one skilled in the art can set the culture period using "the estrogen inhibitor" according to the timing of oocyte cyst breakdown and the follicle formation in each animal species. In addition to usage of the "estrogen inhibitor", it is preferable to set the period for the culture "under conditions that eliminate the effects of sex steroid hormone (for example, estrogen or a factor having a similar function to estrogen)" to the period the period for the completion of the oocyte cyst breakdown and the follicle formation. The culture under such conditions can start from the onset of the oocyte cyst breakdown or can stop before fully completing primary follicle formation.

The culture period for forming the secondary follicle from the primordial germ cell can set depending on the animal species from which the primordial germ cell for the culture derived. It is preferable to take into account the period for forming the secondary follicle from the primordial germ cell in a living body as a guideline of the culture period. When a mouse oocytes is cultured, it is preferable to culture the oocyte until the day corresponding to around 10 days after birth. For example, when the oocyte collected from the fetal female mouse at 12.5 dpc is used for the culture, it is preferable to culture the oocyte for from 15 days to 18 days. When the aggregate of a PGCLC derived from the mouse pluripotent stem cell and the somatic cells is cultured, it is preferable to culture the aggregate for from 11 days to 21 days counting from the onset of the culture of the aggregate preliminary produced.

The estrogen inhibitor and the sex steroid hormone inhibitor can be used to add to a known basal medium for the culture of the primordial germ cell. Such basal medium comprises, for example, α-MEM, PRMI1640, 199, StemPro-34 SFM, and a serum or a serum replacement can be added into those basal medium. The basal medium which can be used for the step (a) of this invention is not limited to the above described medium as long as the primordial germ cell can differentiate into the functional oocyte. When ICI182,780 as the estrogen inhibitor is used in the culture for the mouse primordial germ cell, the agent can be preferably add to the medium in a range from 0.01 to 50 μM (final concentration), more preferably in a range from 0.1 to 10 μM (final concentration). One skilled in the art can adjust the timing of addition or the concentration of the estrogen inhibitor depending on the animal species from which the primordial germ cell derived, the basal medium to be used, and the estrogen inhibitor to be used, etc. In the culture period without adding the estrogen inhibitor, the basal medium mentioned above can be used for the culture. The basal medium can arbitrarily include other factors such as ascorbic acid and penicillin unless the factor inhibits the culture of the primordial germ cell to the functional oocyte.

Another embodiment of the culture "under conditions that eliminate the effects of sex steroid hormone (for example, estrogen or the factor having a similar function to estrogen)" is culturing with a serum-free medium. The serum-free medium can be known serum-free medium (for example, the serum-free medium prepared for usage as it is like StemPro® 34 SFM) or can be the serum-free medium prepared with the serum replacement. When the serum-free medium is prepared with the serum replacement, the serum-free medium can be prepared by adding the commercially available serum replacement such SPS (Serum Protein Substitute), KSR (KnockOut Serum Replacement), and SSS (serum substitute supplement) instead of FBS to the basal medium. The serum replacement is preferably SPS or KSR. As the basal medium used for the preparation of the serum-free medium, the known medium such as α-MEM, DMEM, PRMI1640, 199, and StemPro-34 SFM can be used. In the step (a) of this invention, the basal medium which can be used for the serum-free medium is not limited to ones mentioned above as long as the primordial germ cell can differentiate into the functional oocyte. When, for example, SPS is used instead of serum such as FBS in the culture of the mouse primordial germ cell under the conditions that eliminate the effects of sex steroid hormone (for example, estrogen or the factor having a similar function to estrogen), its concentration can be in a range from 5% to 20% (final concentration), more preferably 10% (final concentration). One skilled in the art can adjust the concentration of the serum replacement depending on the animal species from which the primordial germ cell derived, the basal medium to be used, and the estrogen inhibitor to be used. The period for the culture using the serum-free medium can set to the period for the completion of the oocyte cyst breakdown and the follicle formation. During the culture of the primordial germ cell in the step (a), the serum-free medium can be used from beginning to end.

One skilled in the art adjust the timing to change the medium containing serum to the serum-free medium depending on the animal species from which the primordial germ cell derived, the basal medium to be used, and the estrogen inhibitor to be used. The culture in the period without serum-free medium is preferably performed with the above mentioned basal medium supplemented with serum such as FBS. As mentioned above, in the culture of the gonad, the culture can be performed with the serum-free medium from the beginning to end. The basal medium can arbitrarily include other factors such as ascorbic acid and penicillin unless the factor inhibits the culture of the primordial germ cell to the functional oocyte.

In the culture for forming the secondary follicle from the primordial germ cell, the combination of two or more basal mediums as mentioned above can also be used. For example, according to one embodiment of this invention, α-MEM can be used as the basal medium in the former half period of the culture for forming the secondary follicle from the primordial germ cell and StemPro-34 SFM can be used as the basal medium in the latter half period of the culture. Although the formation of the secondary follicle from the primordial germ cell can be typically achieved with one basal medium, it is preferable to change the basal medium because such medium change can enhance the proliferation of the granulosa cell and can make the follicle structure indestructible in isolating the formed secondary follicle. Such effect to enhance the proliferation of the granulosa cell is desirable especially in forming the secondary follicle from the cell aggregate comprising a PGCLC derived from the pluripotent stem cell and the somatic cells derived from the gonad. For example, when two basal mediums, α-MEM and StemPro-34 SFM, is used in the culture of the cell aggregate comprising a PGCLC derived from the mouse pluripotent stem cell and the somatic cells derived from the gonad, α-MEM medium can preferably change to StemPro-34 SFM medium from day 4 to day 8 after the onset of the aggregate culture, more preferably at day 4 after the onset of the culture. Also in the culture of the primordial germ cell derived from the mouse gonad, the culture medium can change at the same period.

In the culture of the primordial germ cell in the step (a), it is preferable to use a known insert membrane such as Transwell®-COL membrane to a culture plate such as a 6-well plate. During the culture, the half amount of the medium used for the culture can replace with a fresh medium every other day. One skilled in the art can arbitrarily select the culture plate, the insert membrane and the timing of medium change etc. depending on, for example, the animal species from which the primordial germ cell for the culture is derived and the like.

The method of this invention can produce the functional GV stage oocyte by further in vitro culturing the secondary follicle obtained by the step (a). Since the secondary follicle obtainable in the step (a) constitutes a gonad or a part thereof or a gonad like tissue or a part thereof, each secondary follicle can be subject to culture after physically isolating the secondary follicles by using tungsten and the like and cultured.

In the method of this invention, In vitro culture of the secondary follicle includes (b) a step of partially dissociating cells between the granulosa cell layer and a thecal cell layer in which the oocyte, the granulosa cell layer, and the thecal cell layer that constitute the produced secondary follicle. In the secondary follicle obtained by the step (a), the oocyte has the structure surrounded by the granulosa cell layer, which is further surrounded by the theca cell layer. In step (b), the granulosa cell layer and the theca cell layer constituting the follicle are partially dissociated.

Dissociation between the granulosa cell layer and the theca cell layer can be performed by enzyme treatment and/or physical treatment. In a preferable embodiment, the layers can be dissociated by the combination of enzyme treatment and physical treatment.

An embodiment using mouse will be explained below as an example. Regarding the enzyme treatment to dissociate cells between the granulosa cell layer and the theca cell layer in the mouse secondary follicle, the treatment of the mouse secondary follicle, for example, can be performed by treating with L15 medium containing 0.1% collagenase type-I (Worthington Biochemicals, 295 u/mg) for 15 mins at 37° C. To dissociate cells between the granulosa cell layer and the theca cell layer physically, for example, pipetting with a glass capillary or a pipette can be performed. Dissociation between the granulosa cell layer and the theca cell layer can be performed in an extent that all or a part of the theca cell layer can be detached from the follicle.

Partial dissociation between the granulosa cell layer and the theca cell layer enables the medium to penetrate into the portion in which the cell layers are dissociated, and the medium can directly reach to the granulosa cell. While, in the experiment using the primordial germ cell derived from a mouse living body and not performing a step of partial dissociation between the granulosa cell layer and the theca cell layer as the step (b), no functional oocyte could be obtained. The treatment to dissociate cells between the granulosa cell layer and the theca cell layer is preferably performed from day 0 to day 7 from the onset of the follicle culture, more preferably from day 2 to day 4 of the culture. It is preferable not to perform the treatment to dissociate cells between the granulosa cell layer and the theca cell layer soon after the isolation of the secondary follicle and preferable to perform the pre-culture for about 1 to 3 days, and such embodiment enables the follicle to adhere to insert membrane and can make the follicle more stable. The medium for the pre-culture can be the same medium used for the step (c). In a preferred embodiment, GDF9 and/or BMP15 can be added to the medium for the pre-culture. Adding those compounds to the medium for the pre-culture of the secondary follicle can further enhance the proliferation of the granulosa cell, although it is not necessary to add those compounds. In the pre-culture of the mouse secondary follicle, for example, α MEM medium can contain GDF9 and/or BMP15 in a range from 10 ng/ml to 20 ng/ml.

Although the embodiment using mouse was explained above, one skilled in the art can arbitrarily adjust the experimental conditions such as the timing of partial dissociation between the granulosa cell layer and the theca cell layer and the concentration and the period for the enzyme treatment depending on the animal species from which the primordial germ cell derived, the basal medium to be used, and the enzyme to be used.

The method according to this invention in in vitro culture of the secondary follicle, comprises (c) a step of differentiating the oocyte into a functional GV stage oocyte by culturing the oocytes, the granulosa cell layer, and the thecal cell layer that constitute the secondary follicle in the medium containing the high-molecular-weight compound after the step (b) mentioned above.

In in vitro culture of the secondary follicle according to this invention, the medium prepared by adding the high-molecular-weight compound to the basal medium is used. The basal medium includes known medium for the culture of germ cell line, such as α-MEM, DMEM, PRMI1640, and 199. In addition to the high-molecular-weight compound, the basal medium may have the modifications appropriate for the culture cell. For example, the basal medium can arbitrarily contain Fetal bovine serum (FBS), Follicle Stimulating Hormone (FSH), and the like.

In the step (c) according to this invention, the "high-molecular-weight compound" added to the medium is an organic compound having from several tens of thousands to several million molecular weights, and it includes both of natural polymer (biopolymer etc.) and synthetic polymer. In particular, the "high-molecular-weight compound" used for this invention is preferably ones which have the property, for example, of high solubility to water, of extremely low toxicity, of not destabilizing pH and the like in the medium during the culture, and that its original property is remained stable for a long period.

The high-molecular-weight compound used for this invention includes, for example, synthetic polymer, polysaccharide, protein, proteoglycan, and the like. The synthetic polymer includes, for example, polyvinylpyrrolidone (PVP; about 360,000 molecular weights) and polyvinyl alcohol (PVA; about 70,000 to 100,000 molecular weights). The polysaccharide includes, for example, Dextran, hydroxyethylated starch, and derivative of cellulose (for example, hydroxypropyl methylcellulose). Also, the polysaccharide includes, for example, Ficoll® (400,000 molecular weights) which is synthetic polymer of sucrose and glycosaminoglycan such as hyaluronic acid and chondroitin sulfate. The protein includes, for example, serum albumin (about 69,000 molecular weights), and the proteoglycan includes, for example, chondroitin sulfate proteoglycan.

In this invention, the preferable high-molecular-weight compound is not limited to, but PVP, Ficoll®, Hydroxypropyl)methyl cellulose, and serum albumin.

In addition to the above mentioned compounds, the high-molecular-weight compound used for this invention comprises known compounds or compounds to be found or to be synthesized in the future which exhibits the similar property. The compound exhibiting the "similar property" available in this invention is compounds which meet the requirements in using in the culture, that the compound doesn't impair oocyte's survivability, that the somatic cell such as the granulosa cell and theca cell surrounding the oocyte are not peeled away, that the oocyte doesn't lose the oocyte-based structure (no irregular and broad cell proliferation occurs) etc., and which has no effect to the differentiation into the functional oocyte.

The concentration of the high-molecular-weight compound to add is different depending on the animal species of the target oocyte. For example, the compound can be used at the concentration in a range from about 1 to about 12% (w/v) to the basal medium. In mice, the compound can be preferably used at from 1 to 8% (w/v), more preferably from 1 to 4%, most preferably 2% (W/v). In pig and cow, the compound can be preferably used at from 2 to 8% (w/v), more preferably from 2 to 4%, most preferably 4% (W/v).

Although the concentration of the high-molecular-weight is sufficient to accomplish the object in this invention, the concentration in other range may accomplish the object. Concretely, the compound exhibiting high viscosity at a low concentration such as hydroxypropylmethyl cellulose and glycosaminoglycan may be used at the concentration in the other range. For example, in the culture of the porcine or bovine oocyte, the morphology of the complex consisting of the oocyte and the somatic cells in the experiment using a certain type of hydroxypropylmethyl cellulose at 1% (w/v) was a similar to that of the good result of the experiment using PVP (360,000 molecular weights) in a range from 2 to 4% (W/v), which means that such concentration can accomplish the object of this invention.

In fact, the high-molecular-weight compound such as PVP and PVA is commonly used in the medium for the oocyte. In particular, it can be added to the medium not containing the bovine fetal serum or serum albumin as a high-molecular replacement. In this case, it is useful because it can prevent the oocyte from being damaged by avoiding the contact with the bottom surface or the wall surface in the culture plate and with the interior and exterior surface of a fine-drawn glass tube for an embryo operation. The concentration in a range from about 01% to about 0.4% is typically sufficient to accomplish such object, and generally, the concentration is adjusted so as to be in such range. When serum is added to the basal medium, it is often the case that high-molecular-weight compound is not added. By contrast, this invention could elicit the completely different effect by increasing the concentration to from about 1% to about 12%, whereas the conventionally used concentration in the range from about 01% to about 0.4% cannot explicit the effect of the object in this invention. Accordingly, in this invention, depending on the animal species of the target oocyte, it is important to add the high-molecular-weight compound about 2.5 times or more higher than 0.4%, the conventionally used concentration. In the culture of the porcine or bovine oocyte, it is preferable to add the high-molecular-weight compound from about 5 to 10 times or more higher than 0.4%, the conventionally used concentration. In the culture of the mouse oocyte, it is preferable to add the high-molecular-weight compound from about 2.5 to 5 times or more higher than 0.4%, the conventionally used concentration.

The period for the secondary follicle culture in the step (c) can set to the period for forming the functional GV stage oocyte from the oocyte in the secondary follicle, depending on the animal species from which the primordial germ cell for the culture. For example, in mice, in culturing the culture of the secondary follicle obtained by the step (a) by the method in the step (c) can perform, for example, for from 12 days to 16 days, preferably. As mentioned above, the step (b) can be performed at an appropriate timing at or after the onset of the culture of the secondary follicle.

According to this invention, the steps (a) to (c) mentioned above enable the primordial germ cell to differentiate into the functional GV oocyte in vitro.

In this specification, the term "functional GV oocyte" means the GV oocyte (i) having a competency to mature to an egg by in vitro maturation, and (ii) having a competency to develop to normal offspring by fertilizing with a sperm, and (iii) from which the offspring derived has a competency to produce its subsequent normal offspring.

According to one aspect of this invention, the method for producing the functional egg by in vitro maturation culturing the GC oocyte obtained by the in vitro culture of the follicle mentioned above to resume meiosis. In this specification, the term "egg" means the egg reached and suspended at the metaphase stage of the second meiosis (meiosis II). Also, in this specification, the term "functional egg" means the egg (ii) having a competency to develop to normal offspring by fertilizing with a sperm, and (iii) from which the offspring derived has a competency to produce its subsequent normal offspring.

The GV stage oocyte obtained by the in vitro culture of the secondary follicle of this invention can mature to the egg by using the culture method commonly used for in vitro maturation of immature oocyte, and the obtained egg can be used.

For the shift to the maturation culture, generally, COCs collected from the culture plate after completing the culture for oocyte development are rinsed with the medium for the maturation culture and transferred into the finally-used medium for the maturation culture. The maturation medium can be prepared for use by adding essential factors such as sodium pyruvate and antibiotic substance to a known basal medium for the culture of the germ cell line, such as α-MEM and 199, and by further adding gonadotropic hormone, growth factor, serum, follicle fluid, and the like to the medium arbitrarily. The culture conditions preferable for the maturation culture of the oocyte are widely studied and known in the art. An incubator in which the culture plate put can be used under the same conditions to those conventionally used.

The egg matured in this way can be used for a recipient oocyte for the production of a parthenogenetic development embryo or a cloned animal besides the conventional in vitro fertilization.

One aspect of this invention provides a kit for differentiating the primordial germ cell into the functional oocyte or the egg in vitro. The kit according to this invention can include the sex steroid hormone inhibitor (estrogen inhibitor and/or androgen inhibitor), serum-free medium, serum replacement, the enzyme for dissociating cells or the high-molecular weight compound or a combination thereof. In preferable embodiment, the kit includes at least two combination selected from the group consisting of (1) the sex steroid hormone inhibitor (estrogen inhibitor and/or androgen inhibitor), serum-free medium, or serum replacement, (2) the enzyme for dissociating cells, or (3) the high-molecular weight compound. In more preferable embodiment, the kit includes three components of (1) the sex steroid hormone inhibitor (estrogen inhibitor and/or androgen inhibitor), serum-free medium, or serum replacement, (2) the enzyme for dissociating cells, and (3) the high-molecular weight compound. The kit can include other agents or instruments like a culture plate which are necessary for the organ culture or the maturation culture.

This invention will be explained in more detail using examples below. This invention is not limited to the embodiments of the examples described below.

The publications disclosed in this specification will be incorporated by reference.

EXAMPLE

In the examples below, all the animals were purchased from CLEA Japan. BDF1 mouse fetuses were collected from C57BL/6N female mice crossed with DBA/2J male mice at 12.5 dpc. Juvenile and adult female BDF1 mice (C57BL/6N×DBA/2J hybrid) were used for control and male BDF1 mice were used as sperm donors in the examples below. All examples were approved by the Institutional Animal Care and Use Committee of the Tokyo University of Agriculture.
(1. In Vitro Organ Culture of Gonad)

For the medium of the organ culture, the basal medium supplemented with FBS (Gibco, Thermo Fisher Scientific Inc.), SPS (SAGE In vitro Fertilization), the estrogen receptor antagonist, 7α, 17β-[9-([4,4,5,5,5-pentafluoropentyl]sulfinyl)nonyl]estra-1,3,5(10)-triene-3,17-diol; ICI 182,780 (ICI; Tocris Bioscience), 4-hydroxytamoxifen (Sigma-Aldrich), and MPP (Methylpiperidino pyrazole; Cayman Chemical) were added at the indicated concentrations for each experimental group below. The α-MEM medium (Gibco, Thermo Fisher Scientific Inc.) supplemented with 1.5 mM 2-O-α-d glucopyranosyl-1-ascorbic acid (Tokyo Chemical Industry), 10 units/mL penicillin, and 10 μg/mL streptomycin (Sigma-Aldrich) was used as a basal medium (referred to the basal medium hereafter as α-MEM).

ICI 182,780 and 4-hydroxytamoxifen was prepared as follows. ICI 182,780 and 4-hydroxytamoxifen was diluted to 100 mM using DMSO, and cryopreserved stock was prepared. MPP was diluted to 10 mM using DMSO, and cryopreserved stock was prepared. 1 mM solutions of ICI 182,780 and 4-hydroxytamoxifen were prepared by diluting the 100 mM stocks 100-fold with DMSO just before use and were added to the medium at the indicated final concentrations for each experimental group. MPP was added to the medium at 1 μM as the final concentration just before use.

The gonads for the organ culture were collected with mesonephros or without mesonephros from female mouse fetuses at 12.5 dpc (FIG. 1a). 2.2 ml of the medium was added to each 6-well culture plate used for the organ culture. Transwell®-COL membrane (3.0-μm pore size, 24-mm diameter; Corning) was put on each well of the 6-well culture plate. The gonads were transferred on the membrane and were cultured for 17 days at 37° C. under 5% CO2 and 95% air. Approximately half of the medium in each well was replaced with fresh medium every other day. In the example in which the gonad was cultured with mesonephros, mesonephros was removed from the gonad at day 7 of the organ culture.

The in vitro organ culture of the gonads was performed according to the following conditions described below. The gonads were cultured for total 17 days in each conditions below (FIG. 2):

(i) culture for the complete 17 days period in 10% FBS containing α-MEM (α-MEM+FBS; FBS group);

(ii) culture for the complete 17 days period in 10% SPS containing α-MEM (α-MEM+SPS; SPS group);

(iii) culture for the complete 17 days period in 10% KSR containing α-MEM (α-MEM+KSR; KSR group);

(iv) culture in 10% FBS containing α-MEM for 4 days with a shift to 10% SPS containing α-MEM for 6 days from day 5 and a shift to 10% FBS containing α-MEM until day 17 from day 11 (αMEM+FBS/SPS; FBS/SPS group);

(v) culture in 10% FBS containing α-MEM for 4 days with a shift to 10% FBS containing α-MEM with the addition of 10 nM, 100 nM, 1 μM, 5 μM, or 10 μM (final concentration) ICI for 6 days from day 5 and a shift to 10% FBS containing α-MEM until day from day 11 (αMEM+FBS/10 nM ICI; FBS/10 nM ICI group, αMEM+FBS/100 nM ICI; FBS/100 nM ICI group, αMEM+FBS/1 μM ICI; FBS/1 μM ICI group, αMEM+FBS/5 μM ICI; FBS/5 μM ICI group, or αMEM+FBS/10 μM ICI; FBS/10 μM ICI group);

(vi) culture in 10% FBS containing α-MEM for 4 days with a shift to 10% FBS containing α-MEM with the addition of 1 μM (final concentration) 4-hydroxytamoxifen for 6 days from day 5 and a shift to 10% FBS containing α-MEM until day 17 from day 11 (αMEM+FBS/1 μM Tamoxifen; FBS/1 μM Tamoxifen group);

(vii) culture in 10% FBS containing α-MEM for 4 days with a shift to 10% FBS containing α-MEM with the addition of 1 μM (final concentration) MPP for 6 days from day 5 and a shift to 10% FBS containing α-MEM until day 17 from day 11 (αMEM+FBS/1 μM MPP; FBS/1 μM MPP group).

Under the organ culture conditions in each experimental group described above, ovaries were obtained by culturing the gonads. Images of the obtained ovaries under an optical microscope were shown in FIG. 3. In the ovary obtained in (i) FBS group, the boarders between the follicles were unclear, and a part of the theca cell layers was shared with the adjacent follicles and showed an abnormal follicle formation (FIG. 3a). On the other hand, in (ii) SPS group, the abnormalities observed in FBS group were improved (FIG. 3b). Also, the abnormalities were improved in the ovaries obtained in (iv) FBS/SPS group. In the ovaries obtained in (v) FBS/ICI group, the abnormalities were significantly improved, and a round shape of each follicle was clearly observed (FIG. 3d).

Figure 4:
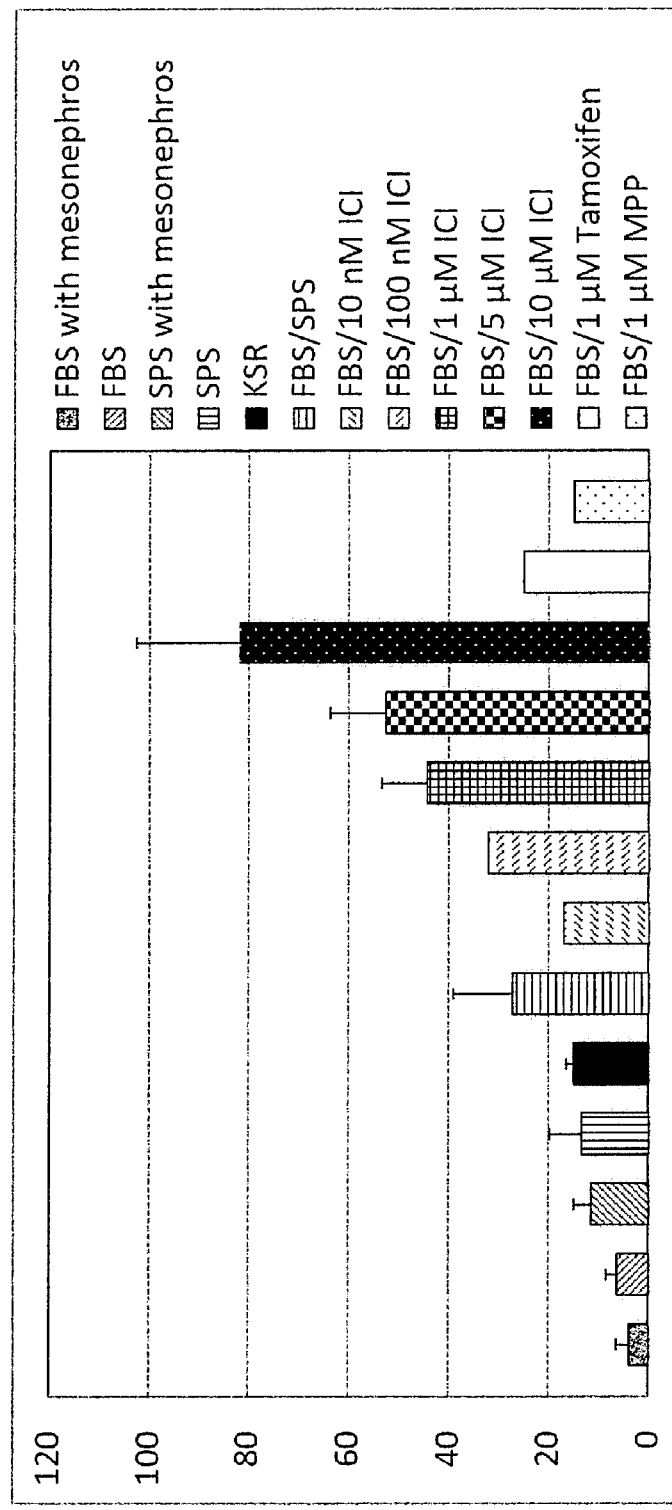
FIG. 4 is the graph showing a comparison of the number of secondary follicles collected from one ovary which was obtained by each of experimental groups in "1. In vitro organ culture of gonad" of the example described below.

Secondary follicles were collected from the ovaries obtained in the in vitro organ culture of the gonads. The number of the secondary follicles obtained from one ovary was compared to each of experimental groups, and FIG. 4 shows its result. In (i) FBS group, only about 4 to 6 secondary follicles were collected from one ovary regardless of mesonephros, whereas in (ii) SPS group, about 12 secondary follicles were collected from one ovary. In (iii) KSR group, about 15 secondary follicles were collected from one ovary. In (iv) FBS/SPS group, 21 secondary follicles were collected from one ovary. On the other hand, in (v) ICI group, the number of the collected secondary ovaries was increased depending on the ICI concentration, and the number of the collected secondary ovaries in each group was significantly increased compared to FBS group (FIG. 4). Similarly, in (vi) FBS/1 µM Tamoxifen group, 25 secondary follicles were collected from one ovary, and in (vii) FBS/1 µM MPP group, 15 secondary follicles were collected from one ovary.

(2. Histological Analysis of Ovary Obtained by In Vitro Culture)

The ovaries cultured for 17 days in (i) FBS group or (v) FBS/10 µM ICI group and the ovaries from female mouse at 10 days after birth were processed for hematoxylin-eosin staining and laminin immunofluorescence staining.

Concretely, the ovaries were fixed for 4 hours at room temperature in 1% paraformaldehyde (PFA)/0.1% glutaraldehyde in 0.05 M phosphate buffer. For H&E staining, the ovaries were embedded in paraffin blocks after a routine protocol, and 4-µm-thick serial sections were prepared. After H&E staining, sections were observed under an IX71 microscope (Olympus). For laminin immunofluorescence staining, ovaries were cut into four to eight pieces, and the tissue sections were incubated for 3 days at 4° C. with an anti-laminin rabbit polyclonal antibody (Abcam) at a dilution of 1:100. Then the tissue sections of the ovaries were incubated for 3 days at 4° C. with an Alexa Fluor 488-conjugated goat anti-rabbit IgG at a dilution of 1:500 (Molecular Probes, Thermo Fisher Scientific Inc.). The obtained tissue sections of the ovaries were further processed for 4',6-diamidino-2-phenylindole (DAPI; Life Technologies) staining. The tissue sections of the ovaries were observed under Zeiss LSM 710 confocal microscope.

Figure 5:
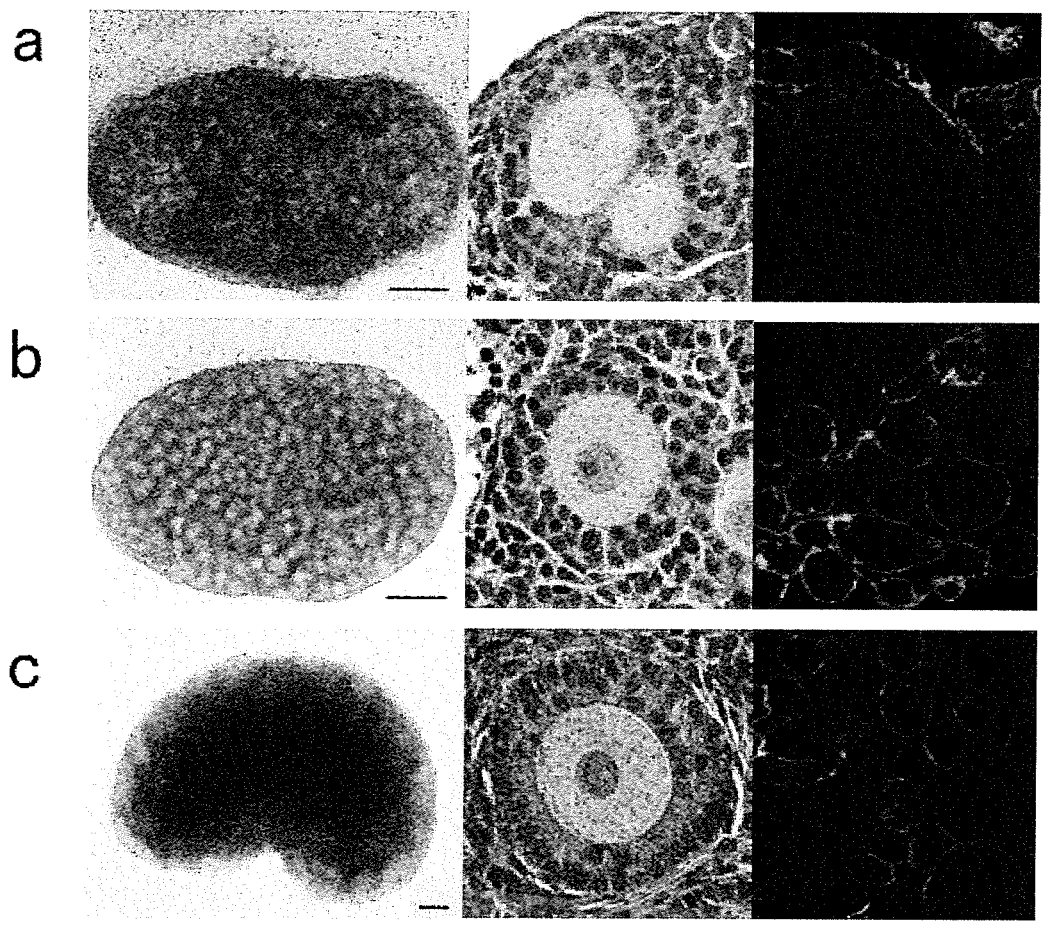
FIGS. 5a and 5b are images of ovaries at day 17 of the culture of (i) FBS group (FIG. 5a) or (v) FBS/10 μM ICI group (FIG. 5b) described in "1. In vitro organ culture of gonad" of the example below, a section thereof, and immunostaining images in which anti-laminin antibody was used.
FIG. 5c is an image of 10-days-old mouse-derived ovary and section thereof, and an immunostaining image in which anti-laminin antibody was used. Bar=100 μm.

The results of hematoxylin-eosin staining and laminin immunofluorescence staining were shown in FIG. 5. In the ovaries in (v) FBS/10 µM ICI group, laminin is circularly localized around the follicle in all aspects on Z-axis in the same manner as oxaries from the female mouse at 10 days after birth. On the other hand, in (i) FBS group, continuously and circularly localized laminin on Z-axis was hardly observed. Although some ovaries of (i)FBS group show circularly localized laminin, multioocyte follicle, a phenomenon that multiple oocytes exist in one follicle, was observed in such ovaries (FIG. 5a). However, in (v) FBS/ICI group, such phenomenon was very few (FIG. 5b). In (v) FBS/ICI group, the same images to the ovaries from the female mouse at 10 days after birth (FIG. 5c) was shown and the follicle formation was improved.

(3. In Vitro Growth Culture of Secondary Follicle)

The secondary follicles obtained by the in vitro organ culture of the gonads from the fetuses was processed for in vitro growth culture. This inventors have revealed that it was effective to add a high-molecular-weight compound to a medium for in vitro growth (IVG) of mouse secondary follicles (Patent literature 1). In this example, the culture was performed with the medium supplemented with PVP which is the high-molecular-weight compound. Furthermore, the inventor found out that oocytes can develop to functional eggs by dissociating a part of the cell layers between a granulosa cell layer and a thecal cell layer which constitute a secondary follicle. Accordingly, in this example, the in vitro culture of the follicle includes a step of partial dissociation between the granulosa cell layer and the thecal cell layer. More concretely, the in vitro culture of the follicle was performed as follows.

After the culture of "1. In vitro organ culture of gonad" for 17 days mentioned above, the cultured gonads (ovaries) were transferred to L15 medium and the secondary follicles formed in the gonads were isolated from the gonads, using a fine Tungsten needle. The secondary follicles were further cultured in α-MEM supplemented with 2% (w/v) PVP, 5% FBS, and 0.1 IU/mL FSH (FOLLISTIM Injection 50; MSD). The secondary follicles were cultured on a Millicell membrane (0.4-µm pore size, 27-mm diameter; Merck Millipore) in a 35-mm culture dish (Falcon, Corning). On day 3 of the culture, the secondary follicles were transferred to 0.1% collagenase type I (Worthington Biochemicals) containing L15 medium and treated for 15 min at 37° C. Then, the theca cell layer of the secondary follicles was removed by pipetting with a pulled fine-glass capillary. Fifty to 60 secondary follicles were cultured on Transwell®-COL or Millicell membranes for another 9 to 13 days at 37° C. in the medium under 5% $CO_2$ and 95% air. The inside and outside of the membrane insert were filled with 1 mL and 2 mL medium, respectively. Approximately half the medium in each well was replaced with fresh medium every other day.

Figure 6:
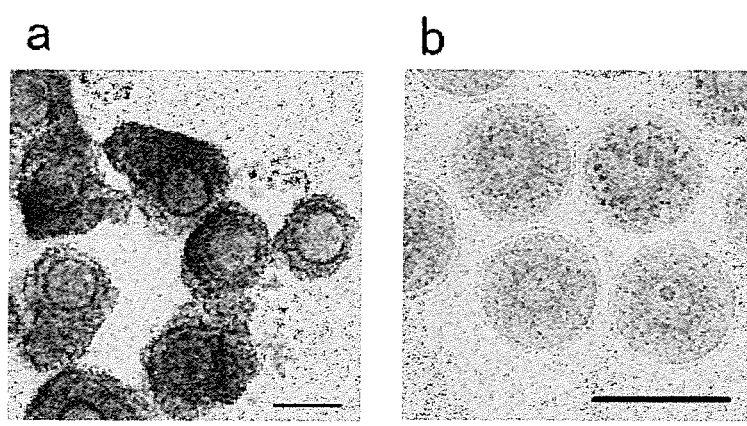
FIG. 6a shows the oocyte-granulosa complexes obtained from follicles at day 12 of the follicle culture (at day 29 from the onset of an organ culture of a gonad).
FIG. 6b shows fully grown oocytes at germinal vesicle (GV) stage (in FIG. 6b, cumulus cells surrounding oocytes are removed).
Figure 7:
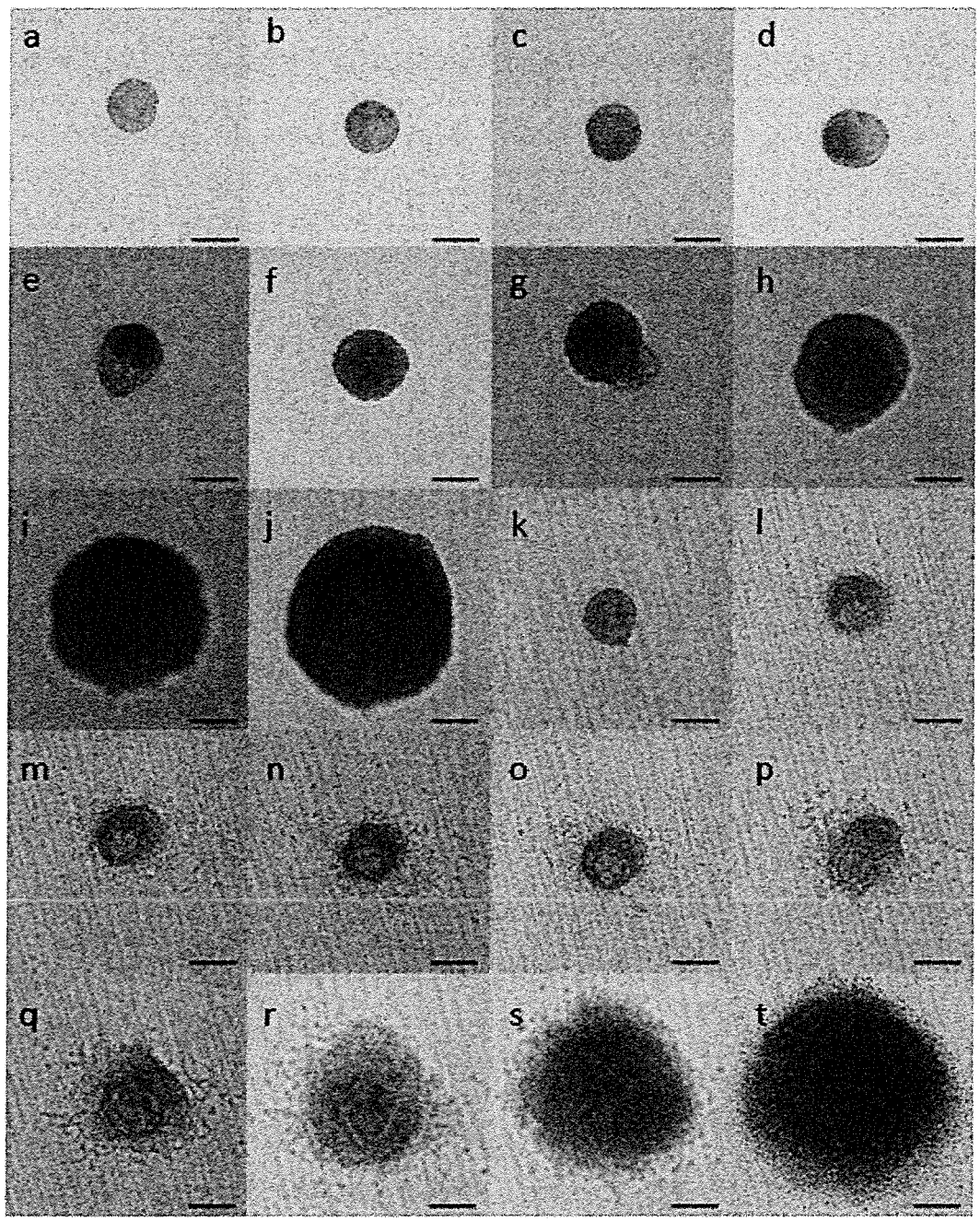
FIGS. 7a to 7j are images of follicles at day 3 to day 12 of the culture on Millicell® membrane in "3. In vitro culture of secondary follicle" described below.
FIGS. 7k to 7t are images of follicles at day 3 to day 12 of the culture on Transwell®-COL membrane in "3. In vitro culture of secondary follicle" described below. The follicles in FIG. 7 are ones obtained by culturing a gonad under the conditions of ICI group. Bar=100 μm.

According to the in vitro culture mentioned above, about 26 to 57% of the follicles which developed from the oocytes of (ii) SPS group, (iv) FBS/SPS group, and (v) FBS/ICI group were sufficiently grown on day 12 to day 16 from the onset of in vitro growth culture of the follicle (the average diameter of the oocytes obtained by the in vitro culture in FBS/10 µM ICI group was 80.0 µm (n=85), the average diameter of the oocytes obtained from a living body was 89.9 µm (n=74)). The developed cumulus-oocyte complexes (COCs) could be isolated from these follicles (FIGS. 6a and 6b, and FIG. 7).

(4. Assessment of Follicle Culture by Hormone Assay)

To assess steroidogenesis during the in vitro culture of the secondary follicles, progesterone and estradiol levels in the medium were measured. More concretely, the secondary follicles obtained by the organ culture of (v) FBS/10 µM ICI group were cultured in the same manner to the in vitro growth culture of the secondary follicles described in the above 3. (Fifty to 60 secondary follicles after collagenase treatment were put on one Transwell®-COL membrane and cultured for 17 days). After day 3 of the in vitro growth culture, half the medium was replaced with fresh medium in every two days. The progesterone and estradiol levels in the medium were measured in duplicate, using an enzyme immunoassay kit (Cayman). The enzyme immunoassay was performed according to the manufacturer's instructions. The result is shown in FIG. 8.

As shown in FIG. 8, progesterone and estradiol levels in the medium was time-dependently increased. This results showed that the secondary follicles in vitro growth cultured according to the method of "3. In vitro culture of secondary follicle" have the same steroidogenic capacity to one which the developing follicles in living body.

(5. DNA Methylation Analysis at Imprinted Loci in Oocyte Obtained by In Vitro Culture of Secondary Follicle)

To assess whether the oocytes obtained by "3. In vitro culture of secondary follicle" described above are the functional oocytes, whether methylation imprints which are necessary for ontogeny were verified to be correctly modified. In particular, the analysis was performed as follows. DNA was isolated from in vitro growth culture derived oocytes at the GV stage which were obtained in FBS/10 μM ICI group and pups developed therefrom. Isolated DNA was then treated with sodium bisulfite (Qiagen) in order to convert unmethylated cytosine to uracil. Sodium bisulfite-treated DNA was subjected to PCR using primers described in Table 1 below.

PCR products were cloned into the pGEM-T Easy vector (Promega) and sequenced on an ABI PRISM 3100 system (Applied Biosystems). At least 20 plasmid DNA clones in each sample were sequenced at each imprinted locus, using QUMA software (Kumaki, Y. et al., "QUMA: quantification tool for methylation analysis." Nucleic Acids Res 36, W170-175, doi:10.1093/nar/gkn294 (2008)).

TABLE 1

| Gene | | Primer Sequence | Size |
|---|---|---|---|
| Igf2r | 1st | 5'-TAG AGG ATT TTA GTA TAA TTT TAA-3' (SEQ ID No: 1)<br>5'-CAC TTT TAA ACT TAC CTC TCT TAC-3' (SEQ ID No: 2) | 549 |
| | 2nd | 5'-GAG GTT AAG GGT GAA AAG TTG TAT-3' (SEQ ID No: 3)<br>5'-CAC TTT TAA ACT TAC CTC TCT TAC-3' (SEQ ID No: 2) | 490 |
| H19 | 1st | 5'-TTT GGG TAG TTT TTT TAG TT-3' (SEQ ID No: 4)<br>5'-TCC TAA TCT CTA ATC TCA AC-3' (SEQ ID No: 5) | 440 |
| | 2nd | 5'-TTT GGG TAG TTT TTT TAG TT-3' (SEQ ID No: 4)<br>5'-AAC CCC AAC CTC TAC TTT TA-3' (SEQ ID No: 6) | 368 |
| Lit1 | | 5'-TAA GGT GAG TGG TTT AGG AT-3' (SEQ ID No: 7)<br>5'-CCA CTA TAA ACC CAC ACA TA-3' (SEQ ID No: 8) | 337 |
| Snrpn | | 5'-AAT TTG TGT GAT GTT TGT AAT TAT TTG G-3' (SEQ ID No: 9)<br>5'-ATA AAA TAC ACT TTC ACT ACT AAA ATC C-3' (SEQ ID No: 10) | 420 |
| Peg1/<br>Mest | | 5'-TTT TAG ATT TTG AGG GTT TTA GGT TG-3' (SEQ ID No: 11)<br>5'-AAT CCC TTA AAA ATC ATC TTT CAC AC-3' (SEQ ID No: 12) | 563 |

The results of DNA methylation analysis were shown in FIGS. 9 and 10. FIG. 9 shows methylation states in oocytes obtained by in vitro culture of this invention, of H19 and Igf2r at the region cloned by the primer sequence shown as $2^{nd}$ in Table 1. FIG. 10 shows DNA methylation states in offspring developed from the oocyte obtained by the in vitro method of this invention (#1 and #2) and DNA methylation states in offspring developed from the GV stage oocytes from adult mice (#3). The results in FIGS. 9 and 10 confirmed that maternal methylation imprints were established in oogenesis even in in vitro culture.

(6. In Vitro Maturation to Egg)

To assess whether the oocytes obtained by "3. In vitro growth culture of secondary follicle" described above complete the meiosis normally, in vitro maturation culture of eggs was performed as follows.

Figure 11:
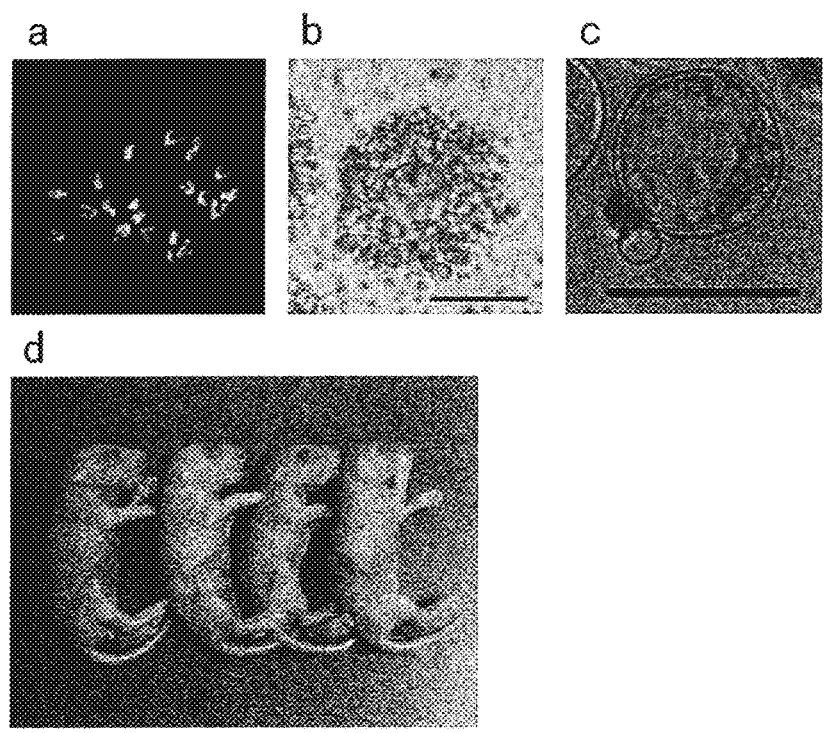
FIG. 11a shows the result of karyotype analysis of oocytes at second meiosis during the culture described in "6. Maturation to egg by in vitro culture".
FIG. 11b shows cumulus-oocyte complexes (COCs) at MII stage obtained in "6. Maturation to egg by in vitro culture" of the example below.
FIGS. 11c and 11d show the image of a blastocyst and offspring obtained by the method in "8. In vitro fertilization of in vitro mature oocyte and embryo transfer" of the example below.

The cumulus-oocyte complexes (COCs) were collected from the secondary follicles obtained by "3. In vitro growth culture of secondary follicle" described above. Then, COCs were cultured with α-MEM containing 5% FBS, 0.1 IU/mL FSH, 1.2 IU/mL chorionic gonadotropin (Gonatropin, ASKA Pharmaceutical), and ng/mL epidermal growth factor (Gibco, Thermo Fisher Scientific Inc.) for 17 hours. Control COCs were collected from adult female mice 44 hours after the injection with equine CG (Serotropin; ASKA Pharmaceutical). The obtained COCs obtained from the adult female mice, in vivo-derived COCs, were cultured with α-MEM containing 5% FBS, 0.1 IU/mL FSH, 1.2 IU/mL chorionic gonadotropin, and 4 ng/mL epidermal growth factor in the same way to in vitro-derived COCs. As a result of in vitro maturation, in (ii) SPS group, (iv) FBS/SPS group, and (v) FBS/ICI group, 77 to 95% oocytes released the first polar body after 17 hours and became MII oocytes (FIGS. 11b and c).

(7. Karyotype Analysis)

To assess whether the oocytes normally entered meiosis during in vitro maturation culture, oocytes processed for karyotype analysis as follows. The fully grown oocytes in second meiosis were incubated in 0.6% sodium citrate for 5 min at room temperature and then spread on glass slides with Carnoy's solution. Chromosomes were stained with DAPI, and the karyotype was analyzed using a Zeiss LSM 710 confocal microscope (Carl Zeiss). As a result of karyotype analysis, oocytes was haploid (N=20) and their meiosis normally progressed (FIG. 11a).

(8. In Vitro Fertilization and Embryo Transfer with in Vitro-Mature Egg)

To assess whether the eggs obtained by the method described in the above "6. In vitro maturation to egg" have the developmental competence to offspring, in vitro fertilization and embryo transfer of in vitro-matured eggs were performed.

After 17 hours of the culture, the eggs with expanded cumulus cells were transferred into TYH medium (LSI Medience Corporation) and fertilized with epididymal sperm. In (ii) SPS group, (iv) FBS/SPS group, (v) FBS/ICI group, about 27 to 58% of eggs which processed for in vitro fertilization (IVF) were normally fertilized. Normally fertilized eggs with 2 pronuclei were cultured in KSOM medium. About 83 to 97% Embryos from the fertilized eggs developed to the 2-cell stage. The embryos developed to the 2-cell stage by the culture were transferred into the oviducts of pseudopregnant females at 0.5 dpc. Offspring were delivered by natural means or by caesarean section at 19.5 dpc. As a result, about 14 to 40% of the transferred embryos developed to offspring. The obtained offspring were raised by foster mothers. The offspring were weaned at about 4 weeks of age. This result shows that this method could produce offspring at high efficiency in spite of using the primordial germ cell from the fetal stage as a starting material. As mentioned above, there has been no report that eggs obtained by in vitro culture in which the primordial germ cell was used as the starting material developed to offspring. Although there is a report that offspring were obtained from eggs which were obtained by culture of non-growth phase oocytes from newborns, the results in this specification was significantly high to the previously reported percentage (about 5.7%) of the offspring developed from transferred embryos. In in vitro culture method for producing the functional egg from the primordial germ cell according to this invention, seven pups from one ovary were obtained at a maximum, and on average, 0.3 to 3.3 pups were obtained from one ovary. Pups were physically normal, and they developed normally. Male and female mice developed from eggs differentiated and matured in in vitro culture could produce the offspring after sexual maturation (Table.

Figure 12:
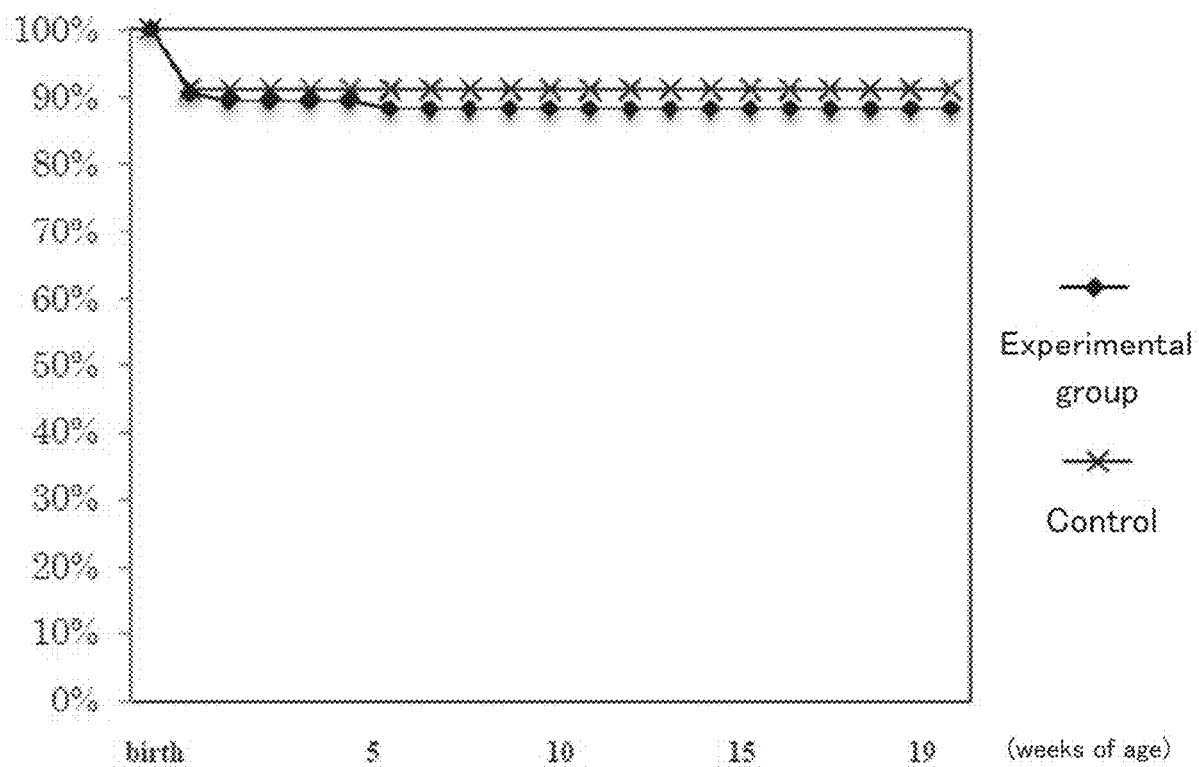
FIG. 12 is the graph showing the comparison between the survival rates of offspring obtained by the method in "8. In vitro fertilization of in vitro mature oocyte and embryo transfer" of the example below and offspring developed from living body-derived oocytes.

2 and FIG. 12). Table 3 shows the sex ratio (Table. 2a) and the birth weight ratio (Table. 2b) of pups obtained in this example (experimental group) to pups obtained by using oocytes from a living body(control).

TABLE 2

|  | ♂ | ♀ |
|---|---|---|
| a | | |
| Experimental group | 48.8% | 51.2% |
| Control | 43.5% | 56.5% |
| b | | |
| Experimental group | 1.53 ± .53 8 g | |
| Control | 1.63 ± .63 8 g | |

(9. Vitrification and Warming)

To assess whether the method for differentiating the primordial germ cell into the functional oocyte and egg according to this invention can apply to the fetal-derived gonads processed for cryopreservation or vitrification, the following experiments were conducted.

Vitrification and warming were conducted as follows by reference to Wang, X. et al., "Successful in vitro culture of pre-antral follicles derived from vitrified murine ovarian tissue: oocyte maturation, fertilization, and live births." Reproduction 141, 183-191 (2011). Gonads collected from female fetuses at 12.5 dpc were dissected into two to three pieces. Gonadal tissues were immersed in 2 mL solution 1, which consisted of L15 medium containing 4 mg/mL BSA (Sigma-Aldrich), 10% (v/v) ethylene glycol (Wako), and 10% (v/v) DMSO (Sigma-Aldrich). Twenty minutes later, gonadal tissues were transferred to 2 mL solution 2, consisting of L15 medium containing 4 mg/mL BSA, 17% (v/v) ethylene glycol, 17% (v/v) DMSO, and 0.75 M sucrose (Wako). Three minutes later, gonadal tissues were placed into cryotubes (Iwaki, Asahi Glass Co.) with 3 µL solution 2 and preserved in liquid nitrogen. To warm the vitrified gonadal tissues, 1 mL of 0.5 M sucrose solution was added to the cryotube and then mixed by pipetting. The gonadal tissues were then washed sequentially with 0.25 M, 0.125 M, and 0 M sucrose solution every 5 min. Warmed gonadal tissues were subject to the in vitro organ culture under the conditions of FBS/1 µM ICI group in "1. In vitro organ culture of gonad" above, and isolated follicles were subject to in vitro growth culture described in "6. In vitro maturation to egg" above. Then, the obtained oocytes were assessed by the method described in "8. In vitro fertilization and embryo transfer with in vitro-mature egg".

The number of the collected oocytes from a vitrified ovary from gonads (about 14 follicles could be obtained from one ovary) decreased compared to that from a non-vitrified ovary. However, oocytes obtained by in vitro culturing the follicles for 13 to 16 days as mentioned above could differentiate to eggs after in vitro maturation, and the eggs could develop to offspring.

Table 3 shows the result of the comparison on efficiency of the development to offspring from the eggs obtained from the in vitro culture of the primordial germ cell, that from the eggs obtained from the in vitro culture of the secondary follicles, and that from the eggs obtained from the in vitro maturation culture of the oocytes. All experimental groups shown in Table 3 below performed the step (b) of partial dissociation between the granulosa cell layer and the theca cell layer surrounding the oocytes in in vitro culture of the secondary follicles and the step (c) of culturing the complexes of the oocytes and the granulosa cells in the medium containing the high-molecular weight compound after the above dissociation step. As mentioned above, before this application, functional eggs could not be obtained by in vitro culture method in which primordial germ cells were used as a starting material to obtain oocytes. However, according to the method of this invention (SPS group, SPS/FBS group, FBA/1 µM ICI group, FBS/5 µM ICI group, FBS/10 µM ICI group, vitrification FBS/1 µM ICI group), the method could produce offspring at high efficiency from the primordial germ cell as an original material. In Table 3 below, the value of percentages described along with the number of collected COCs, matured oocytes, eggs fertilized normally, embryos developed to 2-cell, or born pups shows each proportion to the number of collected follicles (in GV group (control), the value of the percentage shows a proportion to the number of collected COCs).

TABLE 3

| Ovary culture Experimental group | No. of cultured gonads | No. of collected follicles | No. of collected COCs | No. of oocytes matured into MII | No. of eggs fertilized normally | No. of embryos developed to two-cell | No. of pups developed from embryos | No. of pups from an ovary |
|---|---|---|---|---|---|---|---|---|
| FBS | 10 | 67 | 12 | 8 | 1 | 1 | 0 | 0 |
| | | | 17.9% | 11.9% | 1.5% | 1.5% | 0 | |
| SPS | 6 | 47 | 12 | 11 | 3 | 3 | 1 | 0.2 |
| | | | 25.5% | 23.4% | 6.3% | 6.3% | 2.1% | |
| FBS/SPS | 9 | 216 | 60 | 46 | 18 | 15 | 6 | 0.7 |
| | | | 27.8% | 21.3% | 8.3% | 6.9% | 2.8% | |
| FBS/1 µM ICI | 19 | 641 | 340 | 321 | 168 | 155 | 31 | 1.6 |
| | | | 53.0% | 50.1% | 26.2% | 24.2% | 4.8% | |
| FBS/5 µM ICI | 6 | 312 | 178 | 168 | 94 | 91 | 20 | 3.3 |
| | | | 57.1% | 53.8% | 30.1% | 29.2% | 6.4% | |
| FBS/10 µM ICI | 6 | 505 | 281 | 256 | 148 | 138 | 19 | 3.2 |
| | | | 55.6% | 50.7% | 29.3% | 27.3% | 3.8% | |
| Vitrification FBS/1 µM ICI | 4 | 57 | 39 | 37 | 19 | 15 | 2 | 0.5 |
| | | | 68.4% | 64.9% | 33.3% | 26.3% | 3.5% | |
| GV (control) | 19 | | 155 | 139 | 70 | 67 | 40 | 2.1 |
| | | | | 89.7% | 45.2% | 43.2% | 25.8% | |

(10. In Vitro Culture Method for Producing Functional GV Stage Oocyte and Functional Egg Using PGCLC Derived from Pluripotent Stem Cell)

In this example, experiments were conducted to assess whether the in vitro culture of this invention can produce functional GV stage oocytes and functional eggs from PGCLCs derived from pluripotent stem cell. In this example, the method for producing PGCLCs from ES cells and iPS cells was performed in the same way to the method described in a literature "Hayashi K. et al., 'Reconstitution of the mouse germ cell specification pathway in culture by pluripotent stem cells.' Cell, August 19, 146 (4), 519-32 (2011)" unless otherwise specified. The purification of PGCLCs after inducing the differentiation of pluripotent stem cells, the preparation of somatic cells from fetal gonads, and the production method of aggregates of purified PGCLCs and fetal gonad-derived cells were performed in the same manner to the method described in the literature "Hayashi K., et al, 'Offspring from Oocytes Derived from in vitro Primordial Germ Cell-like Cells in Mice.' Science 338, 971-975 (2012) (Non-patent literature 5)" unless otherwise specified.

<I Materials>
<I-1. ES Cell>

ES cells used in this example were the ES cell line established from Blimp1-mVenus and Stella-ECFP (BVSC) induced mouse (the Jackson Laboratory) blastocysts. Blimp1 is a PGC-like cell (PGCLC) marker gene, and Stella is a PGCLC and oocyte marker gene. Karyotype of ES cells used in this example was that of a female cell having 40 chromosomes (38XX).

<I-2. iPS Cell>

In this example, iPS cells were obtained by inducing Oct4, Sox2, Klf4, and c-Myc to fibroblasts from mouse fetuses at 12 dpc was used (Okita et al., "Generation of Mouse Induced Pluripotent Stem Cells Without Viral Vectors" Science November 7; 322(5903):949-53). The mouse fetuses bearing Blimp1-mVenus and Stella-ECFP was contributed for the iPS cell production of this example.

<I-3. Fetus Gonad Cell>

In this example, aggregates of PGCLCs and gonad-derived somatic cells were produced before in vitro culture for forming secondary follicles derived from PGCLCs. The somatic cells to be aggregated with PGCLCs were collected from male mouse fetuses at 12 dpc. In particular, after surgically isolation of gonads from the mouse fetuses, cells constituting gonads were dissociated by treating with 0.05% trypsin at 37° C. for 10 mins. Then, germ cells derived from fetal gonads were removed by Magnetic activated cell sorting. Magnetic activated cell sorting was performed in the same way to the method in Non-patent literature 5 except for using magnetic beads (Miltenyi Biotec) coated with anti-SSEA1 antibody and anti-CD31 antibody.

<II. Methods>
<II-1. Induction of PGCLC from Pluripotent Stem Cell>

Induction of PGCLCs from ES cells or iPS cells were performed according to the method described in a literature "Hayashi K. et al., 'Reconstitution of the mouse germ cell specification pathway in culture by pluripotent stem cells.' Cell, August 19, 146(4), 519-32 (2011)". ES/iPS cells used for the induction of PGCLCs were cultured in N2B27 medium containing 2i (PD0325901, 0.4 µM: Stemgent, San Diego, Calif.; CHIR99021, 3 µM: Stemgent) and LIF (1000 u/ml) under feeder-free conditions for 2 days (5% CO2, 95% air, at 37° C. The following experiments were performed under the same conditions). Next, ES/iPS cells were differentiated into epiblast-like cells (EpiLCs) by culturing in N2B27 medium containing Activin (20 ng/ml), bFGF (12 ng/ml), and KSR (1%) with a human plasma fibronectin-coated dish for 2 days.

The PGCLCs were induced under a floating condition by culturing EpiLCs in a low-cell-binding 96-well plate (NUNC) in a serum-free medium (GK15; GMEM (In vitrogen) with 15% KSR, 0.1 mM NEAA, 1 mM sodium pyruvate, 0.1 mM 2-mercaptoethanol, 100 U/ml penicillin, 0.1 mg/ml streptomycin, and 2 mM L-glutamine) in the presence of BMP4 (500 ng/ml; R&D Systems), LIF (1000 u/ml; In vitrogen), SCF (100 ng/ml; R&D Systems), and EGF (50 ng/ml; R&D Systems).

To separate differentiated PGCLCs from undifferentiated cells, BV-positive cells, which indicates differentiated PGCLCs, were isolated from the cell population containing PGCLCs induced from ES cells or iPS cells by Fluorescence-activated cell sorting (FACS) with a flow cytometer (Aria II, BD Biosciences).

In the following examples, the term "PGCLC" includes a PGCLC derived from ES cells and a PGCLC derived from iPS cells. The PGCLC derived from ES cells and the PGCLC derived from iPS cells were used in the following examples under the same conditions, respectively.

<II-2. Aggregate Culture of PGCLC and Gonad-Derived Somatic Cell>

Aggregate culture of PGCLCs and gonad-derived somatic cells were performed according to the method described in Non-patent literature 5. In particular, PGCLCs and gonad-derived somatic cells were mixed at a ratio of 1:100 in Retinoic Acid-containing GK15 medium (GMEM with 15% KSR, 1×GlutaMax, 1×penicillin/streptomycin, 100 µM 2-mercaptoethanol, and 1 µM Retinoic Acid). PGCLCs and gonad-derived somatic cells were plating on a low-cell-binding 96-well plate (NUNC) at a proportion in which the number of cells constituting the aggregates is about 5500 cells/well and cultured for 2 days to produce the aggregates of PGCLCs and gonad-derived somatic cells.

<II-3. Production of Secondary Follicle>

Figure 13:
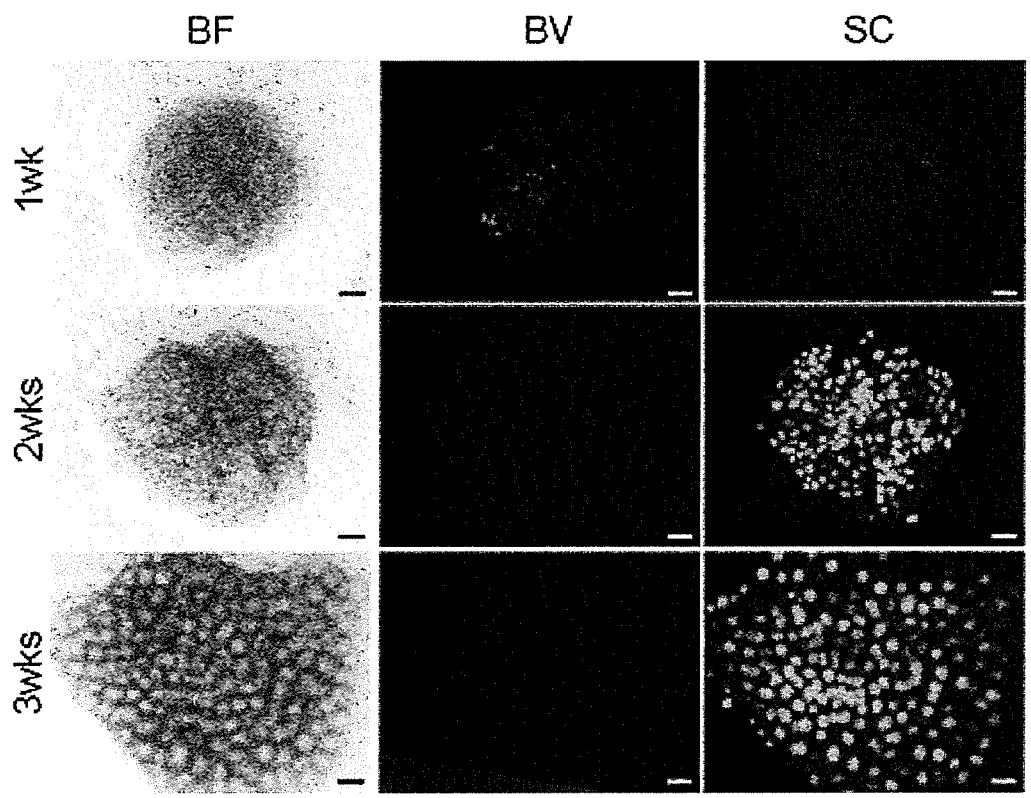
FIG. 13 is the images under an optical microscope (bright field: BF) and the images under fluorescent microscope showing Blimp1 reporter gene (BV; a primordial germ cell marker) expression or Stella reporter gene (SC; a primordial germ cell marker and an oocyte marker) expression on PGCLC derived from ES cells and gonad somatic cells in 1 week, 2 weeks, or 3 weeks after the onset of the culture method described in "II-2. Production of secondary follicle" of "10. In vitro culture method for producing functional GV-stage oocyte and functional egg with PGCLC derived from pluripotent stem cell" described in the example.

The aggregates of PGCLCs and gonad-derived somatic cells which were obtained by <II-2. Aggregate culture of PGCLC and gonad-derived somatic cell> above formed secondary follicles by in vitro-culture as follows. In this example, two basal medium were used in the culture of the aggregates of PGCLCs and gonad-derived somatic cells. From day 0 to day 4 of the culture, α-MEM supplemented with fetal 2% calf serum (FCS), 150 µM ascorbic acid, 1× GlutaMax, 1× penicillin/streptomycin, and 55 µM 2-mercaptoethanol (IVD-αMEM medium) was used. From day 5, StemPro-34 SFM (Life technologies) supplemented with 10% FCS, 150 µM ascorbic acid, 1× GlutaMax, 1× penicillin/streptomycin, and 55 µM 2-mercaptoethanol (IVD-SP medium) was used. In the period from day 7 to day 10 of the culture of the aggregates of PGCLCs and gonad-derived somatic cells, IVD-SP medium supplemented with ICI 182, 780(500 nM) was used. The culture for forming secondary follicles from the aggregates of PGCLCs and gonad-derived somatic cells was performed on Transwell®-Col over the entire period, for total 11 to 21 days. As a result, secondary follicles could be observed on about day 9 to day 11 from the onset of the culture of the aggregates of PGCLCs and gonad-derived somatic cells (FIG. 13, bottom line figures). As shown in FIG. 13, in secondary follicles formed on Week 3 from the onset of the culture Blimp1 expression, a primordial germ cell marker gene, was not observed, and strong Stella expression, an oocyte marker gene, was observed.

<II-4. In Vitro Growth Culture of Secondary Follicle>

Production of a cumulus-oocyte complex (COC) was tested by in vitro culturing secondary follicles obtained in <II-3. Production of secondary follicle> as follows.

Figure 14:
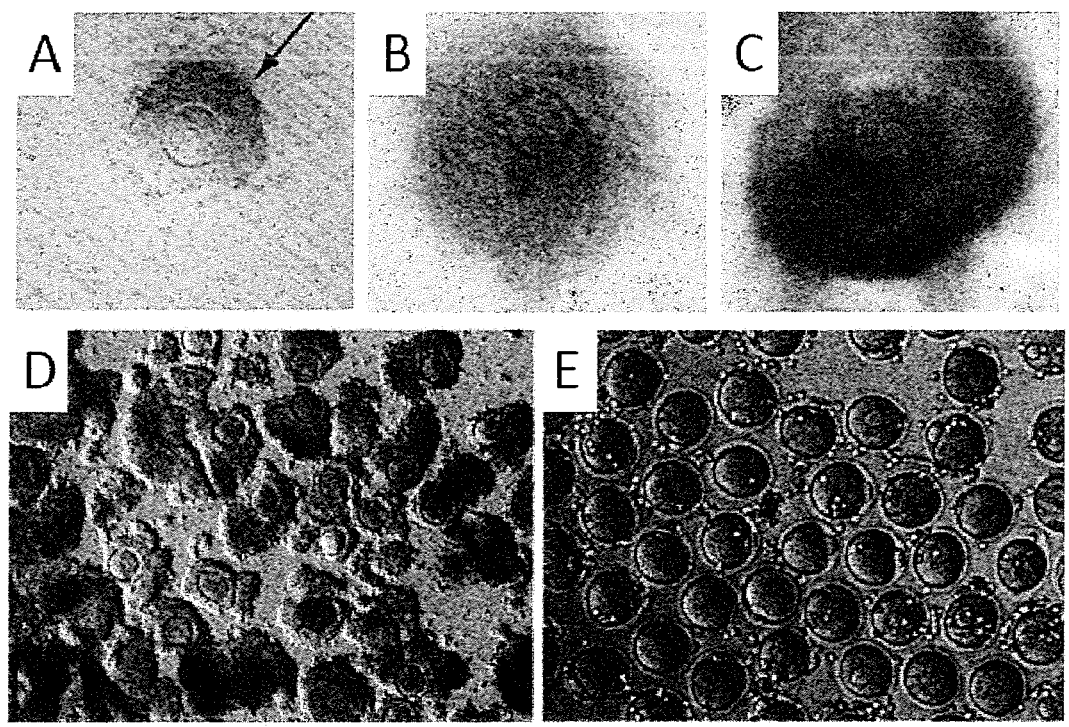
FIG. 14 is images under an optical microscope showing secondary follicle at day 2 (FIG. 14A) or in 1 week (FIG. 14B) or 2 weeks (FIG. 14C) after starting the culture method described in "II-4. In vitro growth culture of secondary follicle" of "10. In vitro culture method for producing functional GV-stage oocytes and functional eggs with PGCLC derived from pluripotent stem cells".

The secondary follicles obtained by the culture was physically isolated with tungsten on Transwell®-Col. The isolated secondary follicles were cultured in IVG medium (α-MEM supplemented with 5% FCS, 2% polyvinylpyrrolidone (Sigma), 150 µM ascorbic acid, 1×GlutaMax, 1× penicillin/streptomycin, 100 μM 2-mercaptoethanol, 55 μg/ml sodium pyruvate, and 0.1 IU/ml FSH) in the presence of GDF9 (15 ng/ml) and BMP15 (15 ng/ml) on Transwell®-Col for 2 days (FIG. 14A). On day 3 of the culture, the secondary follicles were transferred to L15 medium containing 1 mg/ml collagenase type-IV and treated at 37° C. for 25 mins to partially dissociate cells between a granulosa cell layer and a theca cell layer. Then, the secondary follicles were continuously cultured in the above IVG medium without GDF9 and BMP15 on Transwell®-Col (FIG. 14B and FIG. 14C). As a result, COCs could be isolated from the developed secondary follicles with a glass capillary on day 11 (FIG. 14D).

<II-5. In Vitro Maturation to Egg by In Vitro Culture>

COCs obtained in <II-4. In vitro growth culture of secondary follicle> were transferred to IVM medium (α-MEM supplemented with 5% FCS, 25 μg/ml sodium pyruvate, 1× penicillin/streptomycin, 0.1 IU/ml FSH, 4 ng/ml EGF, and 1.2 IU/ml hCG) and cultured for 16 hours. Then, cumulus cells were dissociated from eggs with hyaluronidase, and oocytes released the first polar body were used for in vitro fertilization as MII eggs.

<II-6. In Vitro Fertilization and Embryo Transfer with In Vitro-Mature Egg>

Figure 15:
FIG. 15 shows images new born offspring having normal size of placenta (left figure in FIG. 15) and normal adult mouse grown therefrom (right figure in FIG. 15)

The obtained MII eggs were co-cultured with sperms in IVF medium (HTF supplemented with 4 mg/ml bovine serum albumin). After about 6 hours, the fertilized eggs were transferred to fresh IVF medium and cultured for 1 day. After the culture, embryos developed to 2-cell stage were transferred into the oviducts of pseudopregnant females at 0.5 dpc. Offspring were delivered by caesarean section at day 19 of the transfer. The obtained offspring were raised by foster mothers, and developed to adults. As a result, the offspring developed to physically normal adults (FIG. 15). Furthermore, Male and female mice developed to adults could produce the offspring after sexual maturation. This indicates that the in vitro culture method according to this invention can produce the functional GV stage oocyte and egg from a PGCLC derived from ES cells or iPS cells.

---

The invention claimed is:

1. A method for differentiating a primordial germ cell into a functional GV stage oocyte by in vitro culture, comprising:
   (a) a step of producing a secondary follicle, comprising
      (i) a step of culturing the primordial germ cell and supporting cells adjacent to the primordial germ cell in the presence of serum, wherein the primordial germ cell is derived from a mouse, and
      (ii) a step of culturing the primordial germ cell and supporting cells adjacent to the primordial germ cells obtained in the step (i) in the presence of an estrogen inhibitor or in a serum-free medium, wherein the estrogen inhibitor has the effect of inhibiting the activation of the estrogen receptor;
   (b) a step of partially dissociating cell junctions between a granulosa cell layer and a thecal cell layer of the produced secondary follicle which is constituted with an oocyte, the granulosa cell layer, and the thecal cell layer; and
   (c) a step of differentiating the oocyte into the functional GV stage oocyte by culturing the secondary follicle obtained in step (b) in a medium containing a high-molecular-weight compound.

2. The method according to claim 1, wherein the estrogen inhibitor used in the step (a) is an estrogen receptor antagonist.

3. The method according to claim 1, wherein the partial dissociation of the cell layers in step (b) is carried out by enzymatic treatment and/or by physical means.

4. The method according to claim 1, wherein in the step (c), the high-molecular-weight compound is at least one compound selected from the group consisting of polyvinylpyrrolidone, a synthetic polymer of sucrose and glycosaminoglycan, hydroxypropylmethyl cellulose, and serum albumin.

* * * * *

SEQUENCE LISTING

```
<160> NUMBER OF SEQ ID NOS: 12

<210> SEQ ID NO 1
<211> LENGTH: 24
<212> TYPE: DNA
<213> ORGANISM: artificial sequence
<220> FEATURE:
<223> OTHER INFORMATION: Igf2r 1st forward primer chemically synthesized

<400> SEQUENCE: 1
tagaggattt tagtataatt ttaa                                          24

<210> SEQ ID NO 2
<211> LENGTH: 24
<212> TYPE: DNA
<213> ORGANISM: artificial sequence
<220> FEATURE:
<223> OTHER INFORMATION: Igf2r reverse primer chemically synthesized

<400> SEQUENCE: 2
cacttttaaa cttacctctc ttac                                          24

<210> SEQ ID NO 3
<211> LENGTH: 24
<212> TYPE: DNA
<213> ORGANISM: artificial sequence
<220> FEATURE:
<223> OTHER INFORMATION: Igf2r 2nd forward primer chemically synthesized

<400> SEQUENCE: 3
gaggttaagg gtgaaaagtt gtat                                          24

<210> SEQ ID NO 4
<211> LENGTH: 20
<212> TYPE: DNA
<213> ORGANISM: artificial sequence
<220> FEATURE:
<223> OTHER INFORMATION: H19 forward primer chemically synthesized

<400> SEQUENCE: 4
tttgggtagt tttttagtt                                                20

<210> SEQ ID NO 5
<211> LENGTH: 20
```

```
<212> TYPE: DNA
<213> ORGANISM: artificial sequence
<220> FEATURE:
<223> OTHER INFORMATION: H19 1st reverse primer chemically synthesized

<400> SEQUENCE: 5
tcctaatctc taatctcaac                                              20

<210> SEQ ID NO 6
<211> LENGTH: 20
<212> TYPE: DNA
<213> ORGANISM: artificial sequence
<220> FEATURE:
<223> OTHER INFORMATION: H19 2nd reverse primer chemically synthesized

<400> SEQUENCE: 6
aaccccaacc tctacttta                                               20

<210> SEQ ID NO 7
<211> LENGTH: 20
<212> TYPE: DNA
<213> ORGANISM: artificial sequence
<220> FEATURE:
<223> OTHER INFORMATION: Lit1 forward primer chemically synthesized

<400> SEQUENCE: 7
taaggtgagt ggtttaggat                                              20

<210> SEQ ID NO 8
<211> LENGTH: 20
<212> TYPE: DNA
<213> ORGANISM: artificial sequence
<220> FEATURE:
<223> OTHER INFORMATION: Lit1 reverse primer chemically synthesized

<400> SEQUENCE: 8
ccactataaa cccacacata                                              20

<210> SEQ ID NO 9
<211> LENGTH: 28
<212> TYPE: DNA
<213> ORGANISM: artificial sequence
<220> FEATURE:
<223> OTHER INFORMATION: Snrpn forward primer chemically synthesized

<400> SEQUENCE: 9
aatttgtgtg atgtttgtaa ttatttgg                                     28

<210> SEQ ID NO 10
<211> LENGTH: 28
<212> TYPE: DNA
<213> ORGANISM: artificial sequence
<220> FEATURE:
<223> OTHER INFORMATION: Snrpn reverse primer chemically synthesized

<400> SEQUENCE: 10
ataaaataca ctttcactac taaaatcc                                     28

<210> SEQ ID NO 11
<211> LENGTH: 26
<212> TYPE: DNA
<213> ORGANISM: artificial sequence
<220> FEATURE:
<223> OTHER INFORMATION: Peg1/Mest  forward primer chemically
      synthesized

<400> SEQUENCE: 11
```

```
ttttagattt tgagggtttt aggttg                                26

<210> SEQ ID NO 12
<211> LENGTH: 26
<212> TYPE: DNA
<213> ORGANISM: artificial sequence
<220> FEATURE:
<223> OTHER INFORMATION: Peg1/Mest reverse primer chemically synthesized

<400> SEQUENCE: 12
aatcccttaa aaatcatctt tcacac                                26
```